US008348124B2

(12) United States Patent
Scirica

(10) Patent No.: US 8,348,124 B2
(45) Date of Patent: Jan. 8, 2013

(54) KNIFE BAR WITH GEARED OVERDRIVE

(75) Inventor: Paul Scirica, Huntington, CT (US)

(73) Assignee: Covidien LP, Mansfield, MA (US)

( * ) Notice: Subject to any disclaimer, the term of this patent is extended or adjusted under 35 U.S.C. 154(b) by 59 days.

(21) Appl. No.: 13/023,024

(22) Filed: Feb. 8, 2011

(65) Prior Publication Data

US 2012/0199628 A1    Aug. 9, 2012

(51) Int. Cl.
*A61B 17/068* (2006.01)
(52) U.S. Cl. .................. 227/175.1; 227/180.1; 227/19; 74/89; 74/98; 74/422
(58) Field of Classification Search ............... 227/175.1, 227/180.1, 19; 74/89, 98, 422
See application file for complete search history.

(56) References Cited

U.S. PATENT DOCUMENTS

| | | | |
|---|---|---|---|
| 3,017,637 A | 1/1962 | Sampson | |
| 3,269,630 A | 8/1966 | Fleischer | |
| 3,315,863 A | 4/1967 | O'Dea | |
| 3,548,673 A * | 12/1970 | Suchocki | 74/409 |
| 4,216,891 A | 8/1980 | Behlke | |
| 4,354,628 A | 10/1982 | Green | |
| 4,383,634 A | 5/1983 | Green | |
| 4,506,671 A | 3/1985 | Green | |
| 4,530,453 A | 7/1985 | Green | |
| 4,566,620 A | 1/1986 | Green et al. | |
| 4,568,009 A | 2/1986 | Green | |
| 4,589,582 A | 5/1986 | Bilotti | |
| 4,617,928 A | 10/1986 | Alfranca | |
| 4,665,916 A | 5/1987 | Green | |
| 4,684,051 A | 8/1987 | Akopov et al. | |
| 4,715,520 A | 12/1987 | Roehr, Jr. et al. | |
| 4,788,978 A | 12/1988 | Strekopytov et al. | |
| 4,819,853 A | 4/1989 | Green | |
| 4,869,414 A | 9/1989 | Green et al. | |
| 4,881,544 A | 11/1989 | Green et al. | |
| 4,881,545 A | 11/1989 | Isaacs et al. | |
| 4,915,100 A | 4/1990 | Green | |
| 5,100,042 A | 3/1992 | Gravener et al. | |
| 5,344,060 A | 9/1994 | Gravener et al. | |
| 5,405,073 A | 4/1995 | Porter | |
| 5,452,836 A | 9/1995 | Huitema et al. | |
| 5,465,894 A | 11/1995 | Clark et al. | |

(Continued)

FOREIGN PATENT DOCUMENTS

EP    0 600 182    6/1994

(Continued)

OTHER PUBLICATIONS

European Search Report for EP 11250468.3 dated Aug. 10, 2011.

(Continued)

*Primary Examiner* — Brian D Nash
*Assistant Examiner* — Michelle Lopez

(57) ABSTRACT

A surgical instrument is disclosed. The surgical instrument includes a handle assembly, an elongated portion, an end effector and a drive assembly. The elongated portion extends distally from the handle assembly and defines a longitudinal axis. The end effector is disposed adjacent a distal portion of the elongated portion and includes a first jaw member and a second jaw member. At least one jaw member is movable with respect to the other jaw member between spaced and approximated positions. The drive assembly is disposed in mechanical cooperation with the end effector and includes an input portion, an output portion and a gear system disposed therebetween.

18 Claims, 23 Drawing Sheets

U.S. PATENT DOCUMENTS

| | | | |
|---|---|---|---|
| 5,470,008 A | 11/1995 | Rodak |
| 5,547,117 A | 8/1996 | Hamblin et al. |
| 5,558,266 A | 9/1996 | Green et al. |
| 5,579,978 A | 12/1996 | Green et al. |
| 5,607,094 A | 3/1997 | Clark et al. |
| 5,706,997 A | 1/1998 | Green et al. |
| 5,706,998 A | 1/1998 | Plyley et al. |
| 5,816,471 A | 10/1998 | Plyley et al. |
| 6,805,273 B2 | 10/2004 | Bilotti et al. |
| 6,988,650 B2 | 1/2006 | Schwemberger et al. |
| 7,147,139 B2 | 12/2006 | Schwemberger et al. |
| 7,204,404 B2 | 4/2007 | Nguyen et al. |
| 7,207,472 B2 | 4/2007 | Wukusick et al. |
| 7,434,717 B2 * | 10/2008 | Shelton et al. | 227/176.1 |
| 2005/0006434 A1 | 1/2005 | Wales et al. |
| 2005/0139636 A1 | 6/2005 | Schwemberger et al. |
| 2005/0145672 A1 | 7/2005 | Schwemberger et al. |
| 2005/0247753 A1 | 11/2005 | Kelly et al. |
| 2006/0049230 A1 | 3/2006 | Shelton, IV et al. |
| 2006/0163312 A1 | 7/2006 | Viola et al. |
| 2007/0068990 A1 * | 3/2007 | Shelton et al. | 227/175.1 |
| 2007/0187456 A1 | 8/2007 | Viola et al. |
| 2008/0078800 A1 | 4/2008 | Hess et al. |
| 2009/0114699 A1 * | 5/2009 | Viola | 227/175.1 |
| 2009/0209946 A1 | 8/2009 | Swayze et al. |
| 2010/0072258 A1 | 3/2010 | Farascioni et al. |
| 2010/0213238 A1 | 8/2010 | Farascioni et al. |

FOREIGN PATENT DOCUMENTS

| | | |
|---|---|---|
| GB | 2029754 | 3/1980 |
| WO | WO 02/30296 | 4/2002 |
| WO | WO 2006/055385 | 5/2006 |

OTHER PUBLICATIONS

European Search Report for EP 11178544 dated Sep. 29, 2011.
European Search Report EP 09251240 dated Oct. 5, 2009. (8 pages).
European Search Report for EP 12154328.4-1269 date of completion is May 22, 2012 (6 pages).

* cited by examiner

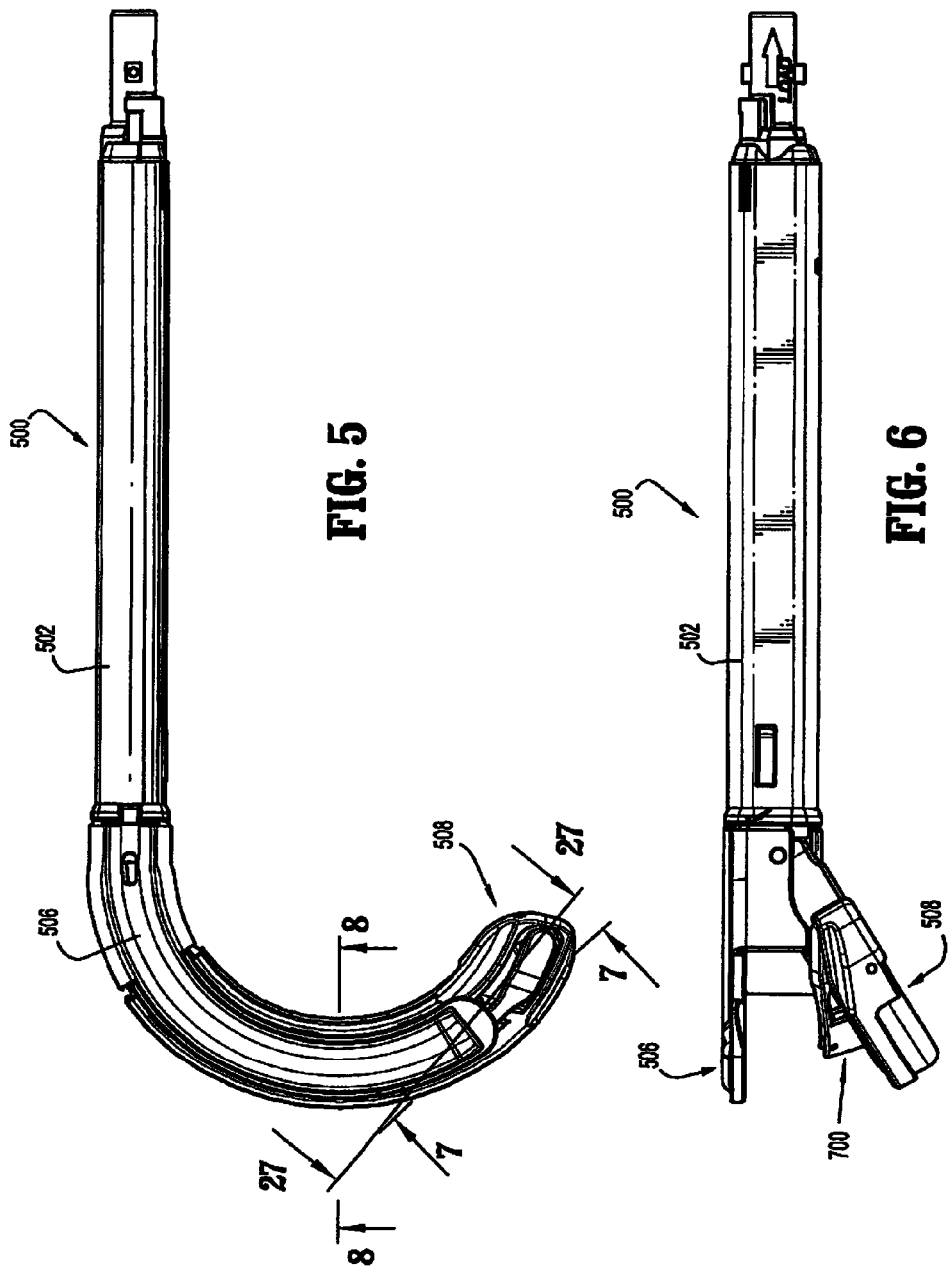

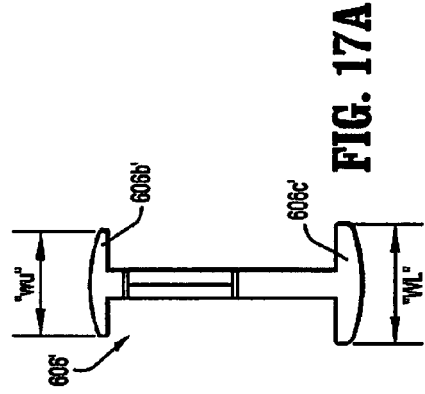
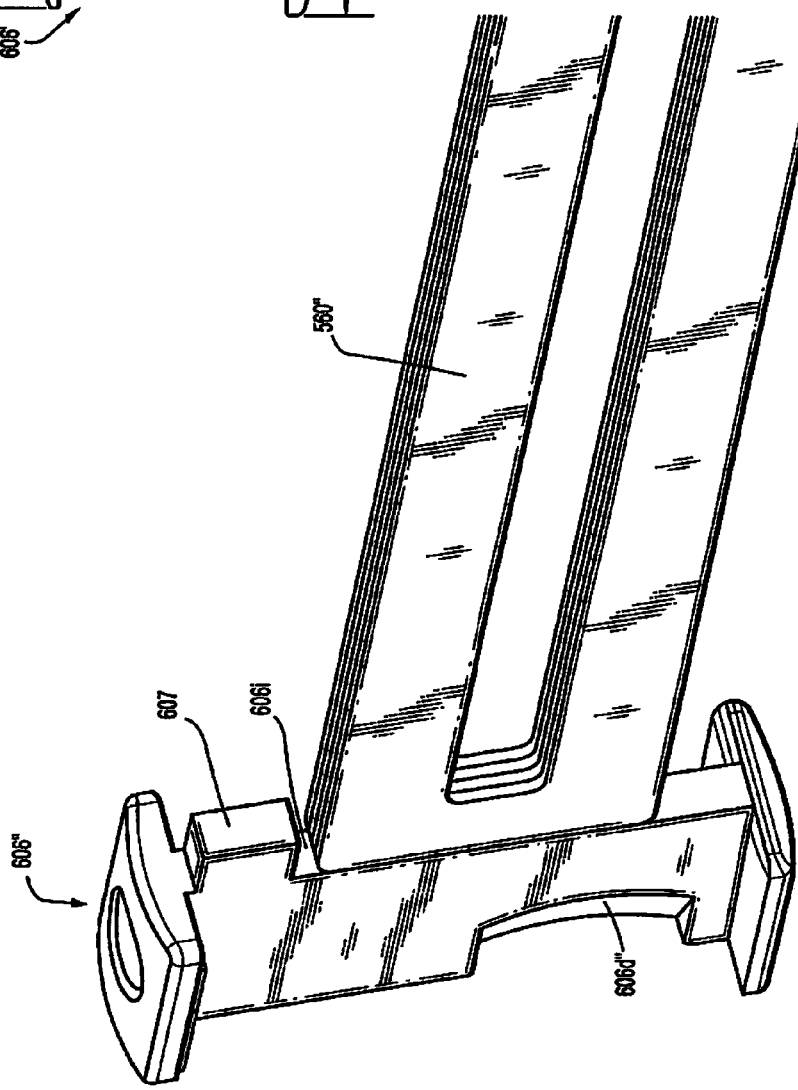

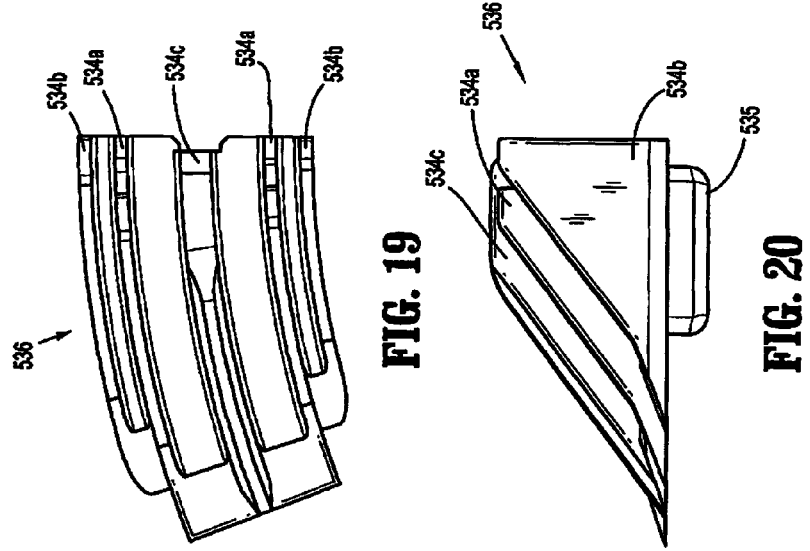
FIG. 19
FIG. 20
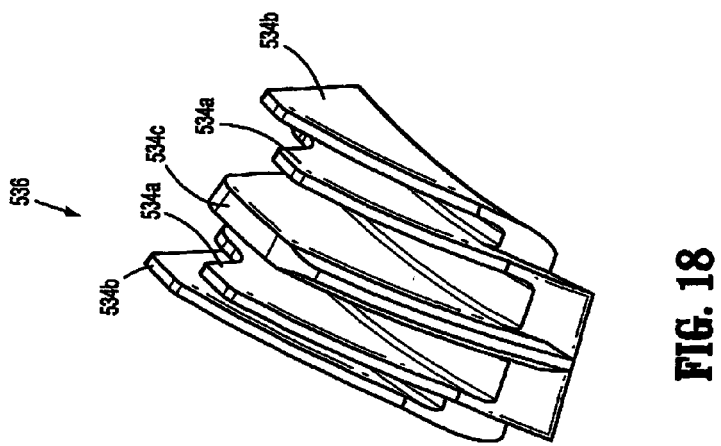
FIG. 18

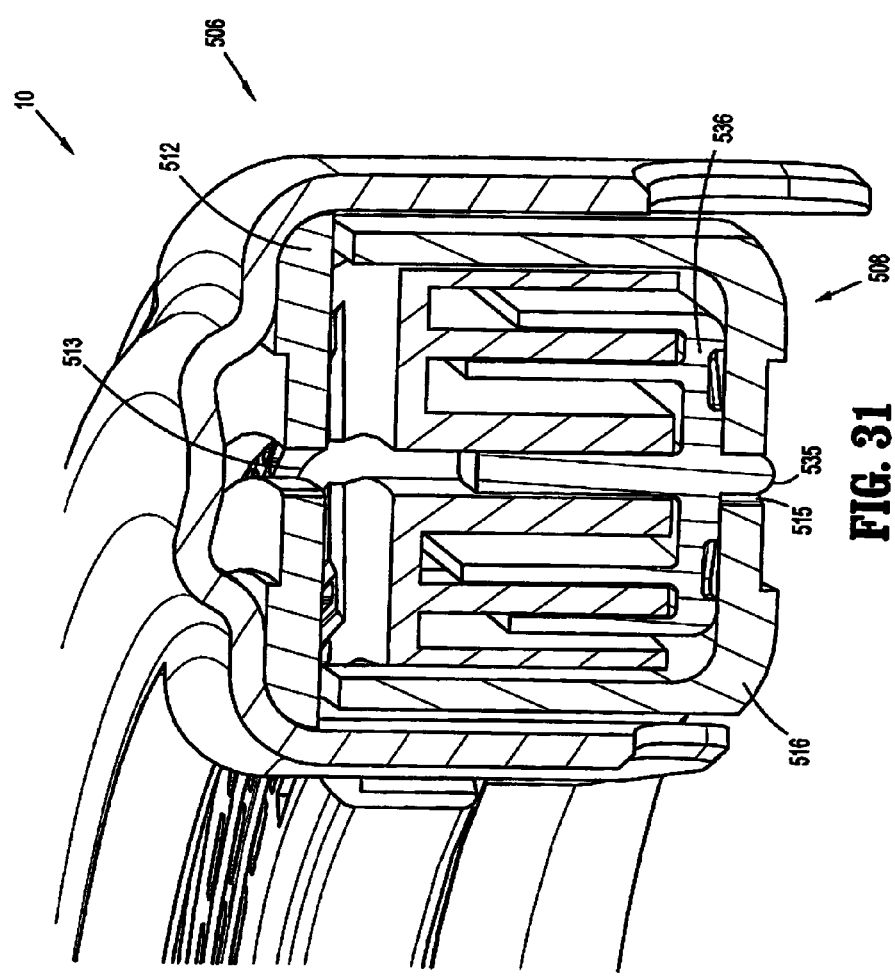

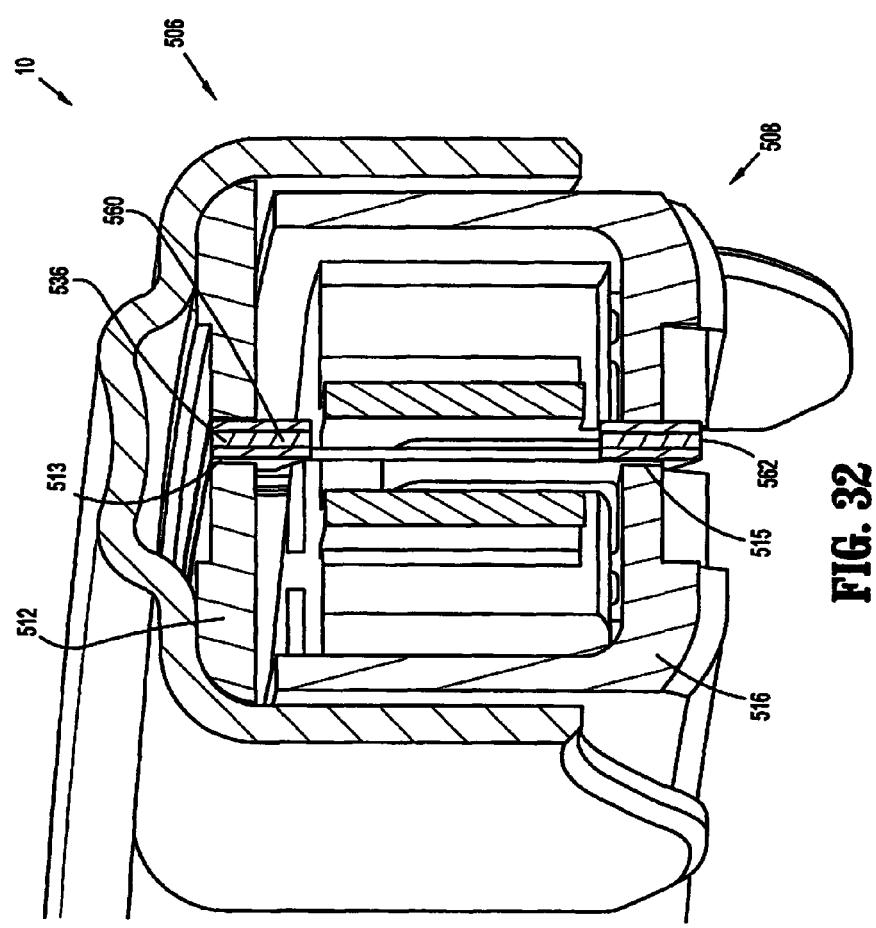

KNIFE BAR WITH GEARED OVERDRIVE

BACKGROUND

1. Technical Field

The present disclosure relates generally to instruments for surgically joining tissue and, more specifically, to surgical instruments having a knife bar including a gear system and loading units for use therewith.

2. Background of Related Art

Various types of surgical instruments used to surgically join tissue are known in the art, and are commonly used, for example, for closure of tissue or organs in transection, resection, anastomoses, for occlusion of organs in thoracic and abdominal procedures, and for electrosurgically fusing or sealing tissue.

One example of such a surgical instrument is a surgical stapling instrument, which may include an anvil assembly, a cartridge assembly for supporting an array of surgical staples, an approximation mechanism for approximating the cartridge and anvil assemblies, and a firing mechanism for ejecting the surgical staples from the cartridge assembly.

Using a surgical stapling instrument, it is common for a surgeon to approximate the anvil and cartridge members. Next, the surgeon can fire the instrument to emplace staples in tissue. Additionally, the surgeon may use the same instrument or a separate instrument to cut the tissue adjacent or between the row(s) of staples.

SUMMARY

The present disclosure relates to a surgical instrument for surgically joining tissue. The surgical instrument includes a handle assembly, an elongated portion, an end effector and a drive assembly. The elongated portion extends distally from the handle assembly and defines a longitudinal axis. The end effector is disposed adjacent a distal portion of the elongated portion and includes a first jaw member and a second jaw member. At least one jaw member is movable with respect to the other jaw member between spaced and approximated positions. The drive assembly is disposed in mechanical cooperation with the end effector and includes an input portion, an output portion and a gear system disposed therebetween.

The surgical instrument may include a longitudinally-extending slot in the second jaw member; an upper portion of the drive assembly is configured and dimensioned to travel at least partially within the longitudinally-extending slot of the second jaw member.

In certain embodiments, the handle assembly is mechanically engaged with a drive rod such that actuation of the a portion of the handle assembly causes distal translation of the drive rod. The input portion of the drive assembly is configured to mechanically engage a distal portion of the drive rod.

In disclosed embodiments, the output portion of the drive assembly is affixed to a dynamic clamping member. The dynamic clamping member is configured to eject fasteners from the first jaw member.

In disclosed embodiments, the input portion of the drive assembly includes a plurality of teeth, and the output portion of the drive assembly includes a plurality of teeth. In disclosed embodiments, the gear system includes an input gear including teeth. Here, the teeth on the input portion of the drive assembly are configured to engage the teeth of the input gear. In disclosed embodiments, the gear system includes an output gear including teeth. Here, the teeth on the output portion of the drive assembly are configured to engage output teeth of output gear.

In disclosed embodiments, the gear system includes a shaft extending through centers of each of the input gear and the output gear.

In disclosed embodiments, the gear ratio of the output gear to the input gear is between about 1.25:1 to about 2:1.

In disclosed embodiments, the end effector is curved with respect to the longitudinal axis.

The present disclosure also relates to a tool assembly for use with a surgical instrument. The tool assembly includes an end effector and a drive assembly. The end effector includes a first jaw member and a second jaw member. The first jaw member is movable with respect to the second jaw member between spaced and approximated positions. The drive assembly is disposed in mechanical cooperation with the end effector, and includes an input portion, an output portion and a gear system disposed therebetween.

In disclosed embodiments, the input portion of the drive assembly is configured to mechanically engage a distal portion of a drive rod of the surgical instrument.

In disclosed embodiments, the output portion of the drive assembly is affixed to a dynamic clamping member, and the dynamic clamping member is configured to eject fasteners from the first jaw member.

In disclosed embodiments, the input portion of the drive assembly includes a plurality of teeth, and the output portion of the drive assembly includes a plurality of teeth.

In disclosed embodiments, the gear system includes an input gear including teeth, and the teeth on the input portion of the drive assembly are configured to engage the teeth of the input gear.

In disclosed embodiments, the gear system includes an output gear including teeth, and wherein the teeth on the output portion of the drive assembly are configured to engage output teeth of output gear.

In disclosed embodiments, the gear system includes a shaft extending through centers of each of the input gear and the output gear.

In disclosed embodiments, the gear ratio of the output gear to the input gear is between about 1.25:1 to about 2:1.

In disclosed embodiments, the end effector includes a longitudinally curvilinear shape.

BRIEF DESCRIPTION OF FIGURES

Various embodiments of the presently disclosed surgical instrument are disclosed herein with reference to the drawings, wherein:

FIG. 5 is a top view of the loading unit of FIGS. 3 and 4;

FIG. 6 is a side view of the loading unit of FIGS. 3-5, illustrated with a cartridge assembly in the open position;

FIG. 17A is a rear view of another embodiment of a dynamic clamping member according to another embodiment of the present disclosure;

FIG. 17B is a perspective view of another embodiment of a dynamic clamping member according to another embodiment of the present disclosure;

FIGS. 18-20 are various views of an actuation sled in accordance with an embodiment of the present disclosure;

FIG. 31 is a perspective transverse cross-sectional view of the surgical instrument taken across a portion of the actuation sled in accordance with an embodiment of the present disclosure; and FIG. 32 is a perspective cross-sectional view of the surgical instrument in accordance with an embodiment of the present disclosure.

DETAILED DESCRIPTION

Figure 1:
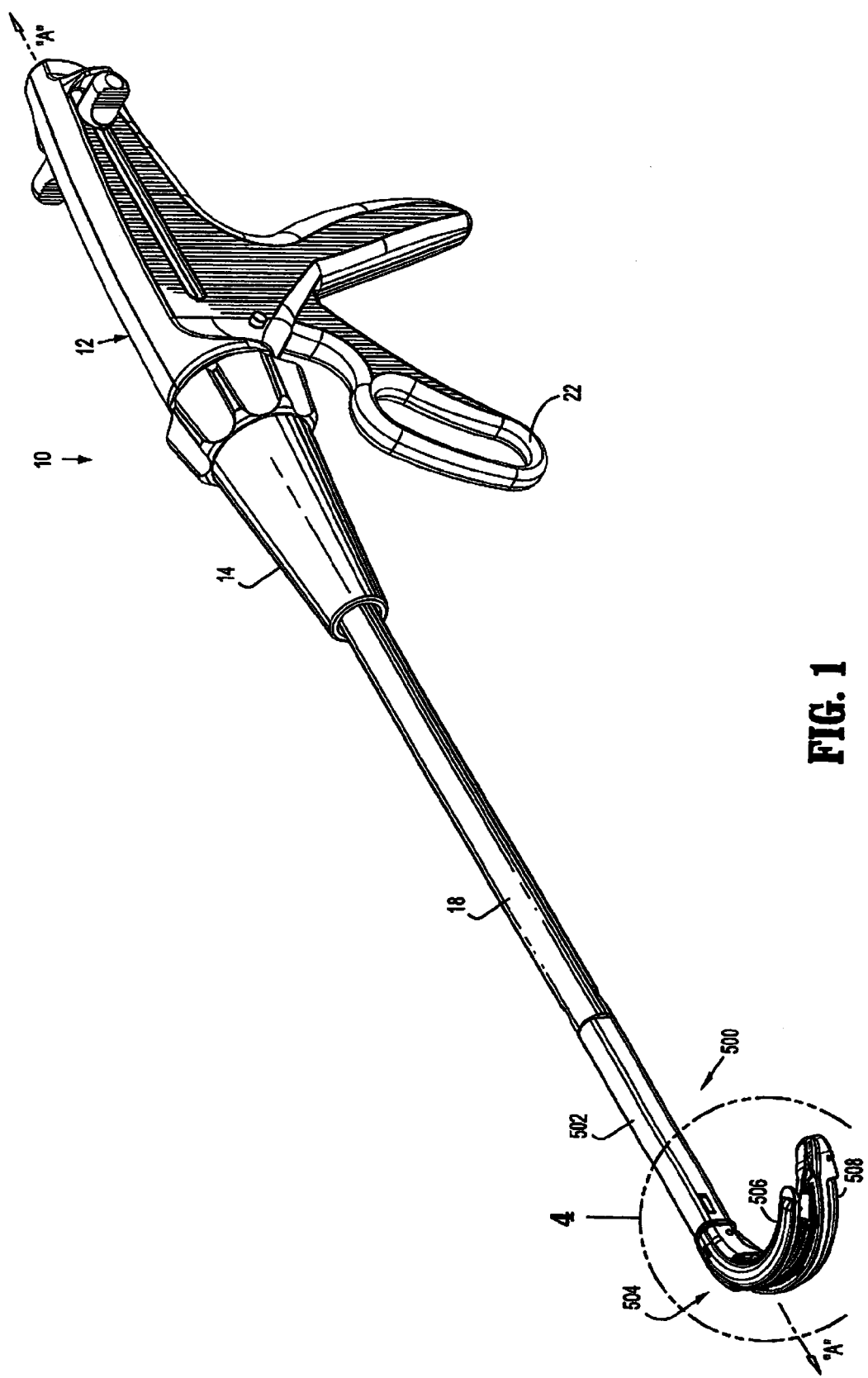
FIG. 1 is a perspective view of a surgical stapling instrument including a loading unit in accordance with the present disclosure.

Embodiments of the presently disclosed surgical instrument, and loading unit for use therewith, are described in detail with reference to the drawings, wherein like reference numerals designate corresponding elements in each of the several views. As is common in the art, the term 'proximal" refers to that part or component closer to the user or operator, e.g., surgeon or physician, while the term "distal" refers to that part or component farther away from the user.

Figure 1A:
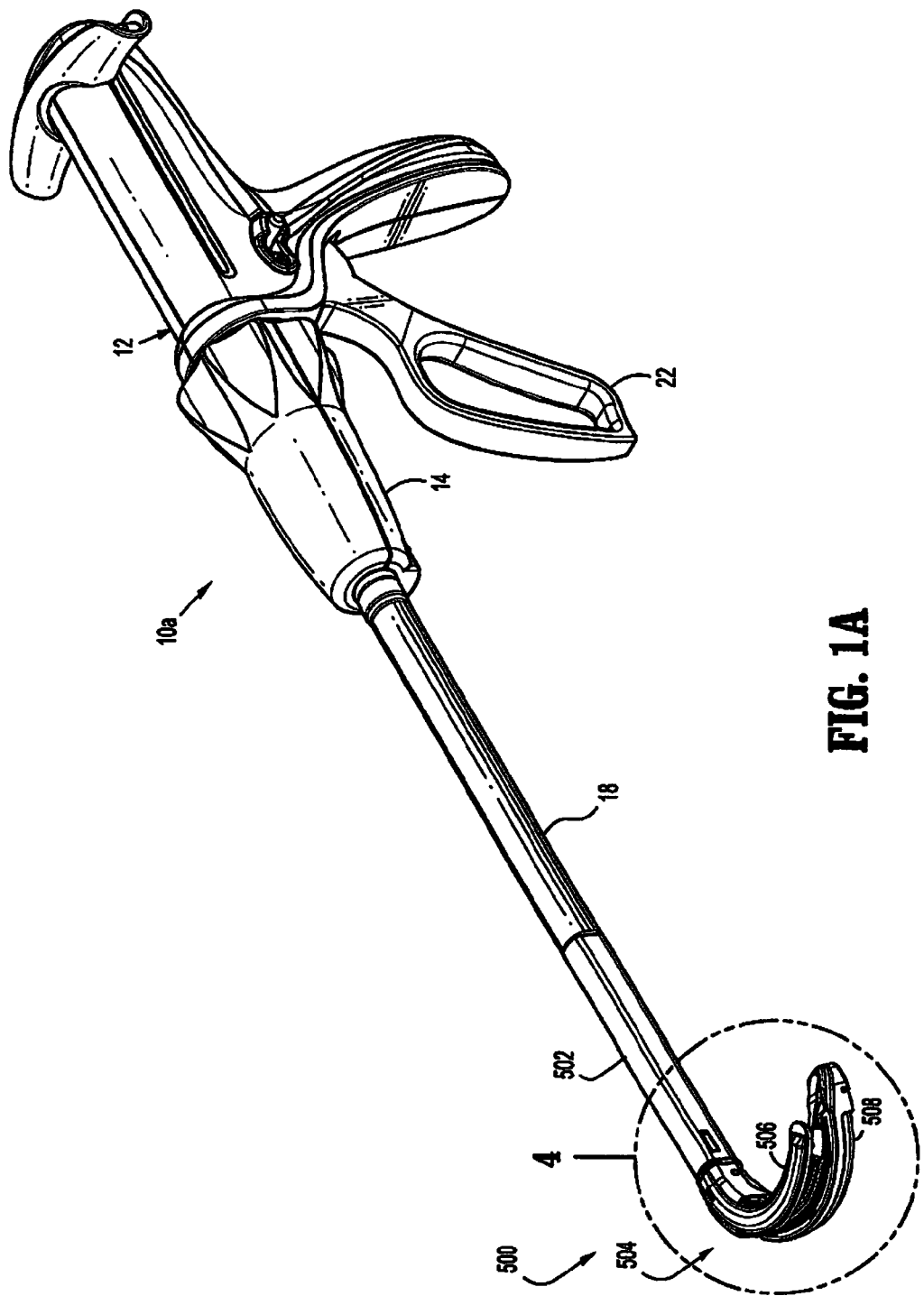
FIG. 1A is a perspective view of another type of surgical stapling instrument including the loading unit of FIG. 1 in accordance with an embodiment of the present disclosure.
Figure 2:
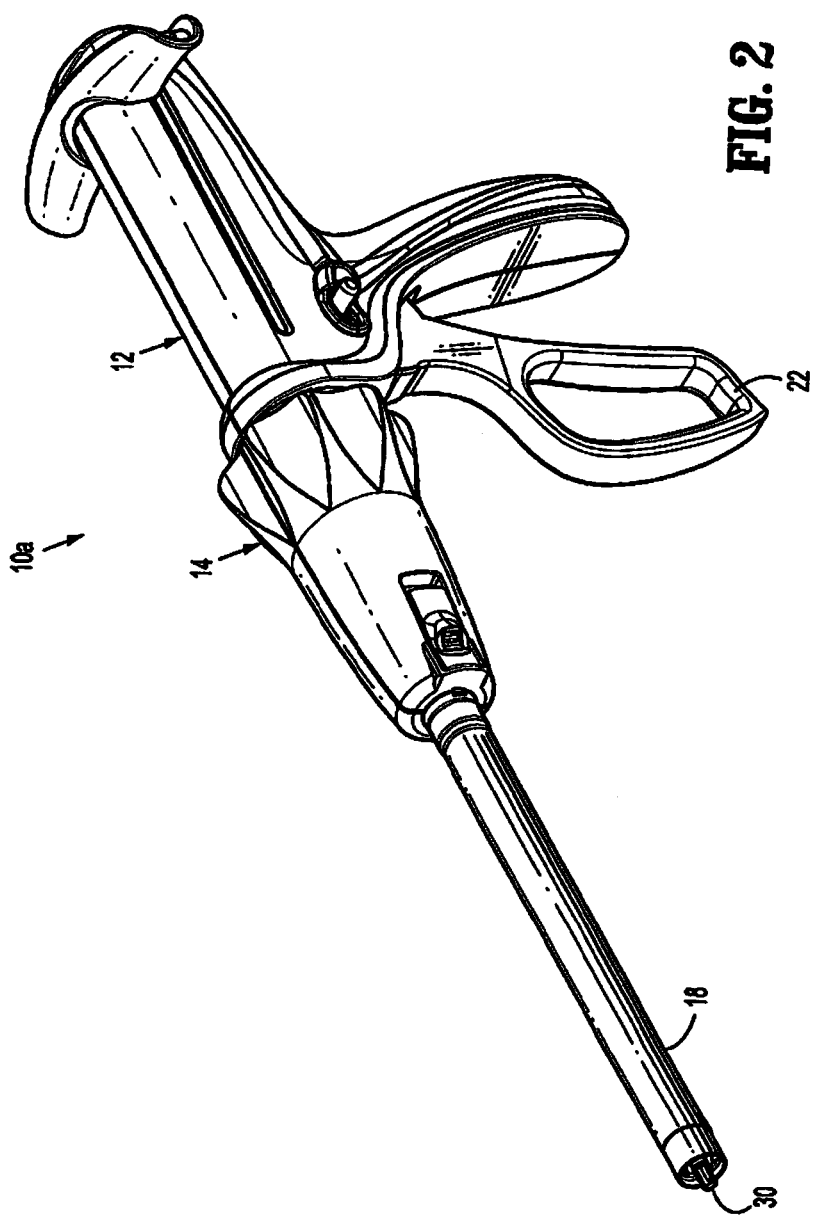
FIG. 2 is a perspective view of a handle assembly of the surgical stapling instrument of FIG. 1A.

A first type of surgical stapling instrument of the present disclosure is indicated as reference numeral 10 in FIG. 1. Another type of surgical stapling instrument of the present disclosure is indicated as reference numeral 10*a* in FIGS. 1A and 2. Additionally, while not explicitly shown, the present application also relates to surgical stapling instruments having parallel jaw members. Collectively, all surgical instruments (including surgical stapling instruments 10 and 10*a*) are referred to herein as "surgical instrument" and referred to as reference numeral 10. Similarly, several features that are common to both surgical stapling instruments are collectively referred to as the same reference number (e.g., handle assembly 12, rotation knob 14, and endoscopic portion 18). Further details of an endoscopic surgical stapling instrument are described in detail in commonly-owned U.S. Pat. No. 6,953,139 to Milliman et al., the entire contents of which are hereby incorporated by reference herein.

A loading unit 500 for use with surgical instrument 10 is shown in FIGS. 3-10 and 28-30. Loading unit 500 is attachable to an elongated or endoscopic portion 18 of surgical instrument 10, e.g., to allow surgical instrument 10 to have greater versatility. Loading unit 500 may be configured for a single use, and/or may be configured to be used more than once. Examples of loading units for use with a surgical stapling instrument are disclosed in commonly-owned U.S. Pat. No. 5,752,644 to Bolanos et al., the entire contents of which are hereby incorporated by reference herein. The loading unit shown includes a proximal body portion that is attachable to an elongated portion of a surgical instrument having a handle assembly. However, the tool assembly can be incorporated in a surgical instrument in which a staple cartridge is removable and replaceable and does not include a detachable portion of the elongated portion of the instrument.

Loading unit 500 includes a proximal body portion 502 and a tool assembly 504. Proximal body portion 502 defines a longitudinal axis "A-A," and is releasably attachable to a distal end of elongated body portion 18 of surgical instrument 10. Tool assembly 504 includes a pair of jaw members including an anvil assembly 506 and a cartridge assembly 508. One jaw member is pivotal in relation to the other. In the illustrated embodiments, cartridge assembly 508 is pivotal in relation to anvil assembly 506 and is movable between an open or unclamped position (e.g., FIGS. 4 and 6) and a closed or approximated position (e.g., FIG. 8). Cartridge assembly 508 is urged in the open position via a biasing member, e.g., a pair of compression springs 533 disposed between anvil cover 510 and cartridge 518 (see FIG. 10).

Figure 10:
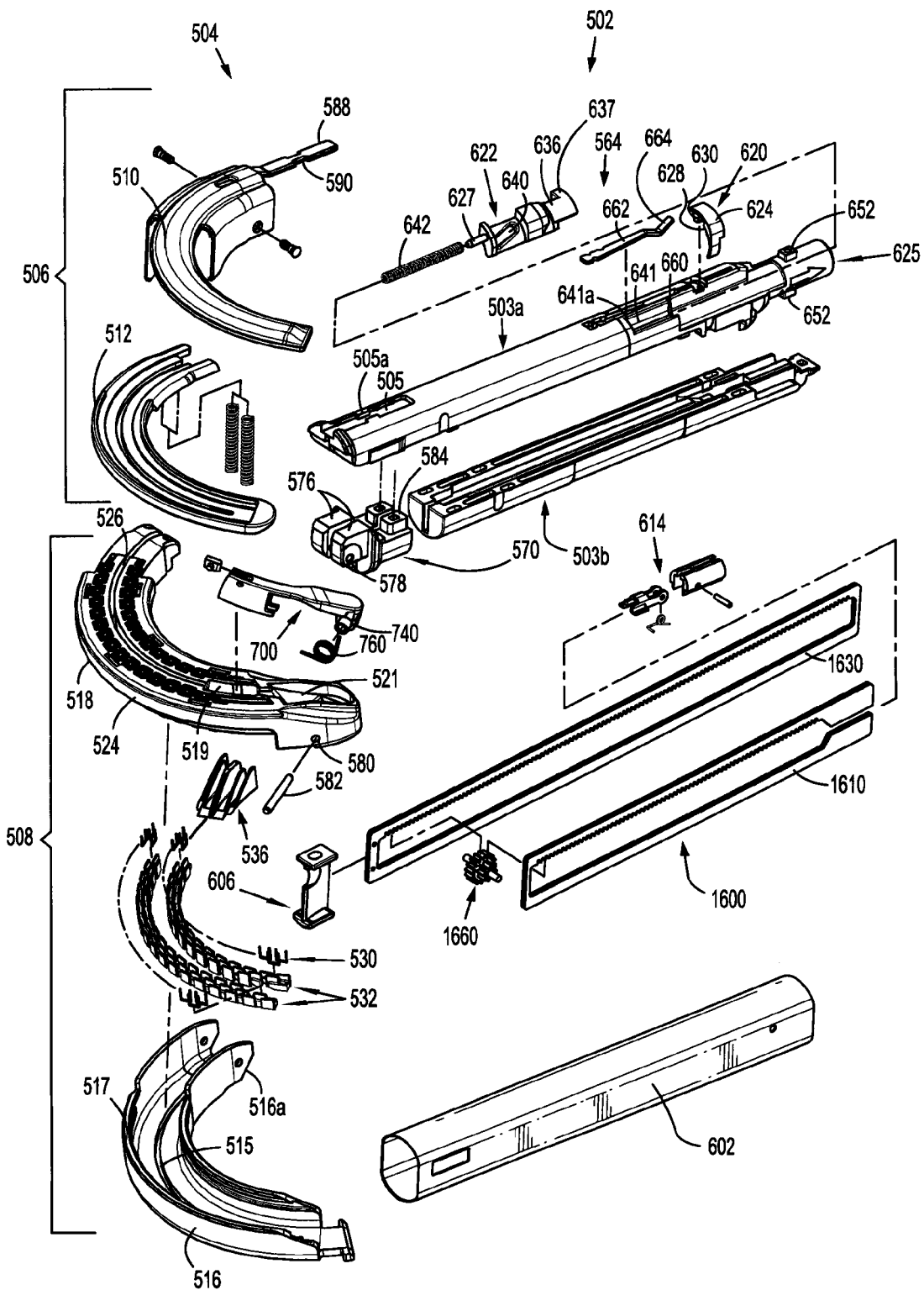
FIG. 10 is a perspective assembly view of the loading unit of FIGS. 3-9.

With reference to FIGS. 1 and 10, for example, tool assembly 504 includes anvil assembly 506 and cartridge assembly 508. As shown, each of anvil assembly 506 and cartridge assembly 508 is longitudinally curved. That is, anvil assembly 506 and cartridge assembly 508 are curved with respect to the longitudinal axis "A-A" defined by proximal body portion 502. As used herein with respect to curved parts of the surgical instrument 10 of the present disclosure, the term "distal," which typically refers to that part or component of the instrument that is farther away from the user, refers to the portion of the curved part that is farthest along an axis that follows the curve of the curved part. That is, while an intermediate portion of a curved part may be farther from the user during use, the portion of the curved part that is farthest along its axis is considered "distal."

In disclosed embodiments, the radius of curvature of both anvil assembly 506 and cartridge assembly 508 is between about 1.00 inches and about 2.00 inches, and in particular, may be approximately 1.40 inches. The curved jaw members, as compared to straight jaw members, may help facilitate access to lower pelvis regions, e.g., during lower anterior resection ("LAR"). Additionally, the inclusion of curved jaw members may allow increased visualization to a surgical site and may also allow more room for a surgeon to manipulate target tissue or the jaw members themselves with his or her hand.

Figure 8:
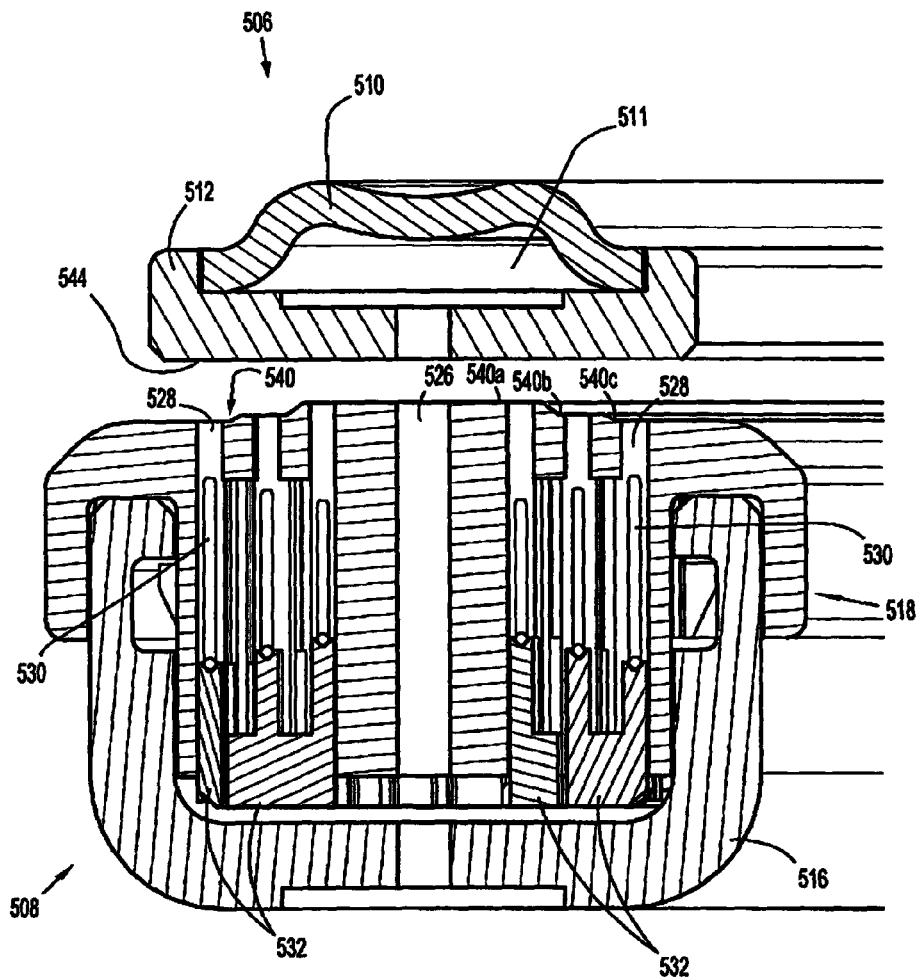
FIG. 8 is a transverse cross-sectional view of the loading unit of FIGS. 3-7.
Figure 9:
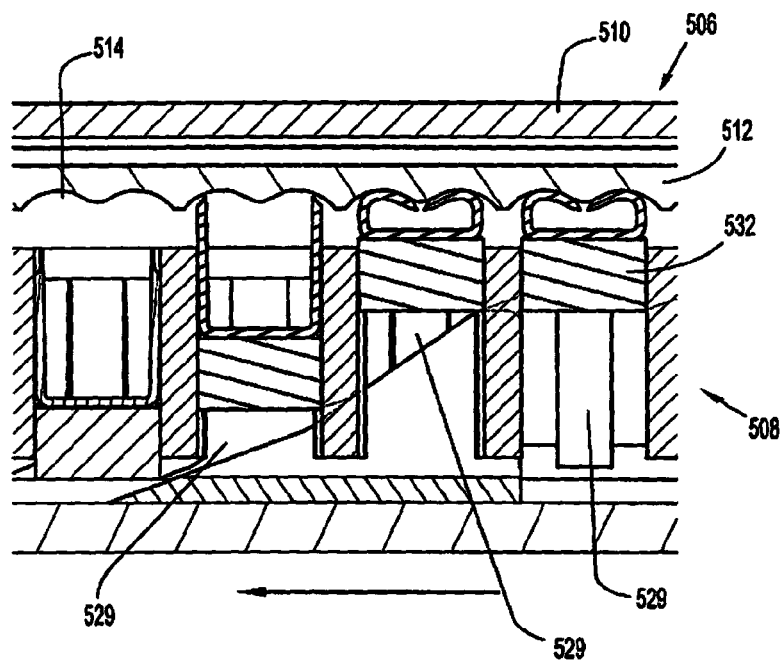
FIG. 9 is a longitudinal cross-sectional view of a portion of the loading unit of FIGS. 3-8.

With reference to FIG. 10, anvil assembly 506 includes a longitudinally curved anvil cover 510 and a longitudinally curved anvil plate 512, which includes a plurality of staple forming depressions 514 (FIG. 9). In disclosed embodiments, the radius of curvature of both anvil cover 510 and anvil plate 512 is between about 1.00 inches and about 2.00 inches, and in particular, may be approximately 1.40 inches. Anvil plate 512 is secured to an underside of anvil cover to define a channel 511 (FIG. 8) between plate 512 and cover 510. When tool assembly 504 is in the approximated position (FIG. 8), staple forming depressions 514 are positioned in juxtaposed alignment with cartridge assembly 508.

Cartridge assembly 508 includes a longitudinally curved channel or carrier 516 which receives and supports a longitudinally curved cartridge 518. The cartridge 518 can be attached to the channel or carrier by adhesives, a snap-fit connection, or other connection. In disclosed embodiments, the radius of curvature of both carrier 516 and cartridge 518 is between about 1.00 inches and about 2.00 inches, and in particular, may be approximately 1.40 inches. Cartridge 518 includes a pair of support struts 524 which rest on sidewalls 517 of carrier 516 to stabilize cartridge 518 on carrier 516. Support struts 524 also set the height or location of cartridge 518 with respect to anvil plate 512. An external surface of carrier 516 includes an angled cam surface 516a.

Figure 7:
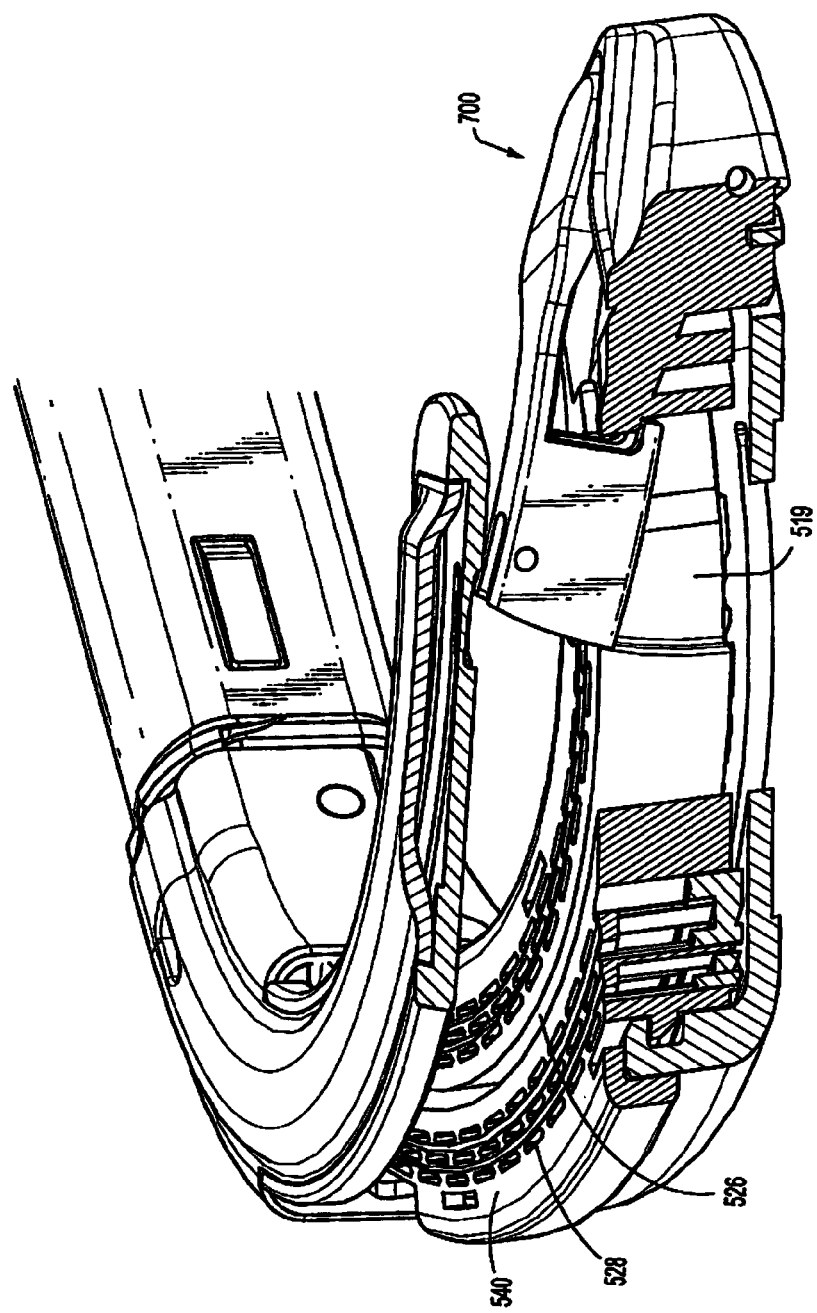
FIG. 7 is a perspective, partial cross-sectional view of the loading unit of FIGS. 3-6.

Cartridge 518 defines a plurality of laterally spaced staple retention slots 528, which are configured as holes in tissue contacting surface 540 (see FIG. 7). Each slot 528 is configured to receive a staple 530 therein. Cartridge 518 also defines a plurality of cam wedge slots 529 (see FIG. 9) which accommodate staple pushers 532 and which are open on the bottom (i.e., away from tissue contacting surface 540) to allow a longitudinally curved actuation sled 536 to pass therethrough.

Staple cartridge 518 includes a central longitudinally curved slot 526, and three longitudinally curved rows of staple retention slots 528 positioned on each side of curved longitudinal slot 526 (see FIGS. 7 and 8). In disclosed embodiments, the radius of curvature of both slot 526 and pusher 532 is between about 1.00 inches and about 2.00 inches, and in particular, may be approximately 1.40 inches. More specifically, actuation sled 536 passes through cam wedge slots 529 and forces staple pushers 532 towards respective staples 530. The staples are then forced out of their respective staple retention slots 528.

Figure 21:
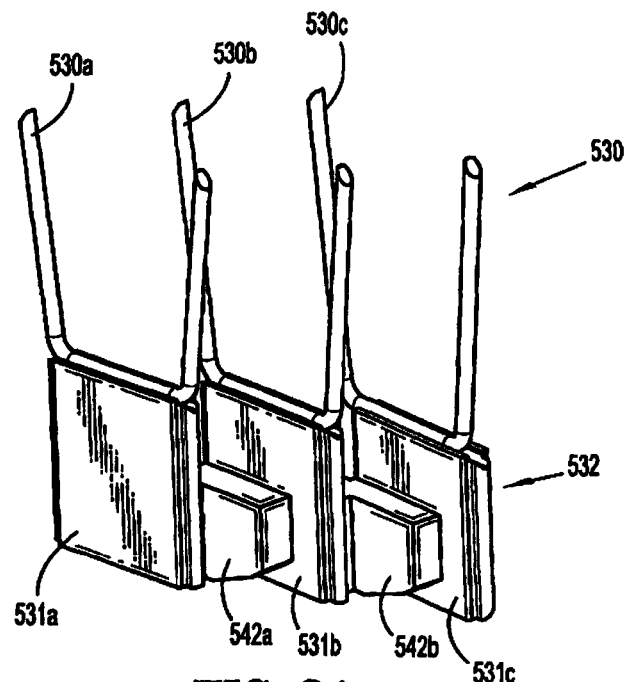
FIGS. 21 and 22 are perspective views of staples and staple pushers in accordance with embodiments of the present disclosure.
Figure 22:
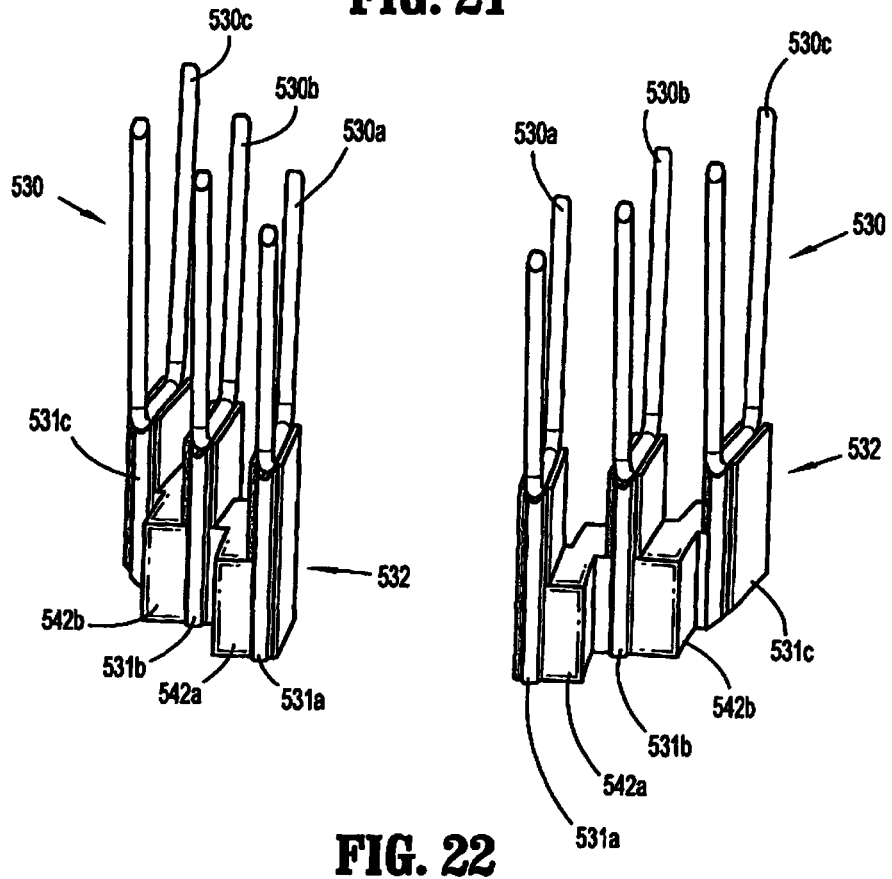
Figure 23:
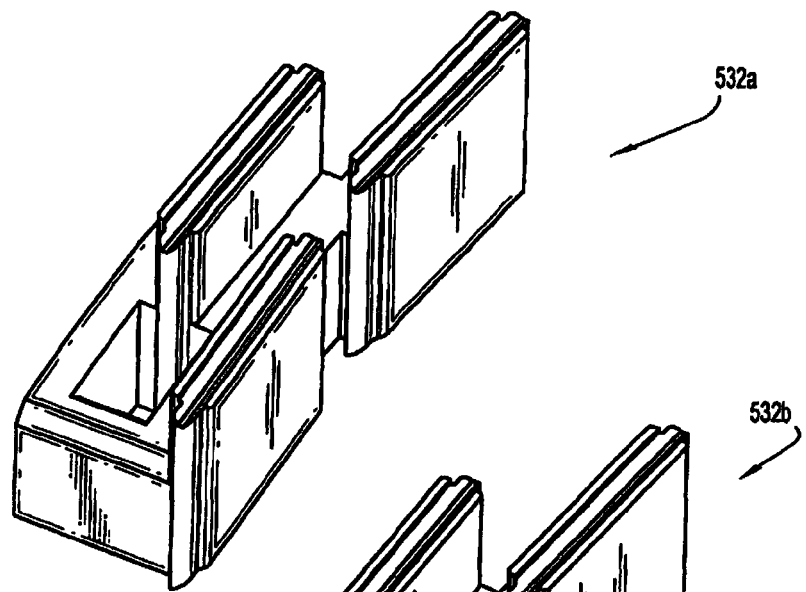
FIGS. 23-25 are perspective views of various staple pushers in accordance with embodiments of the present disclosure.
Figure 24:
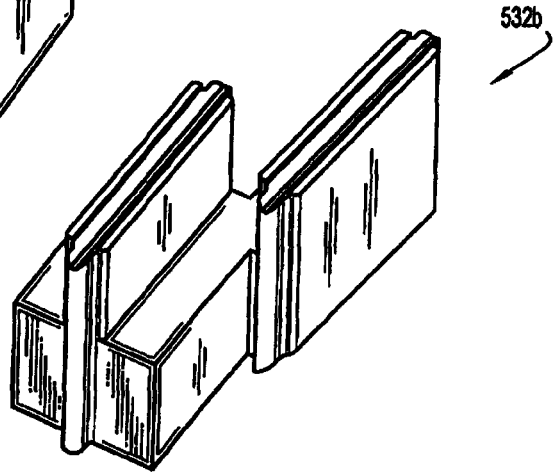
Figure 25:
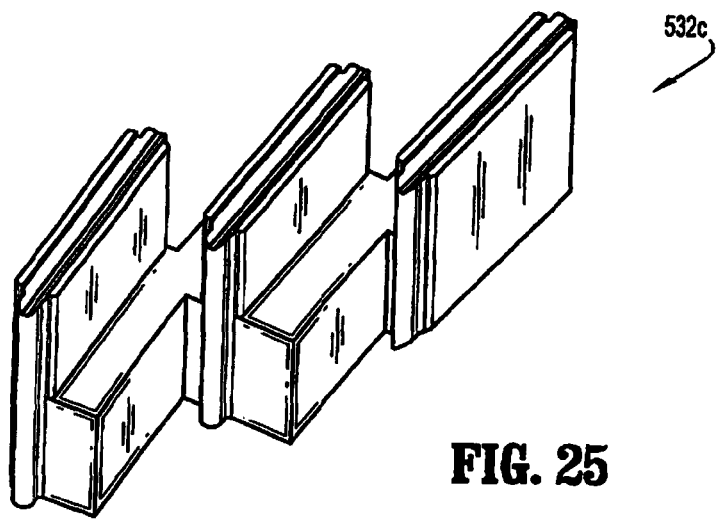
Figure 27:
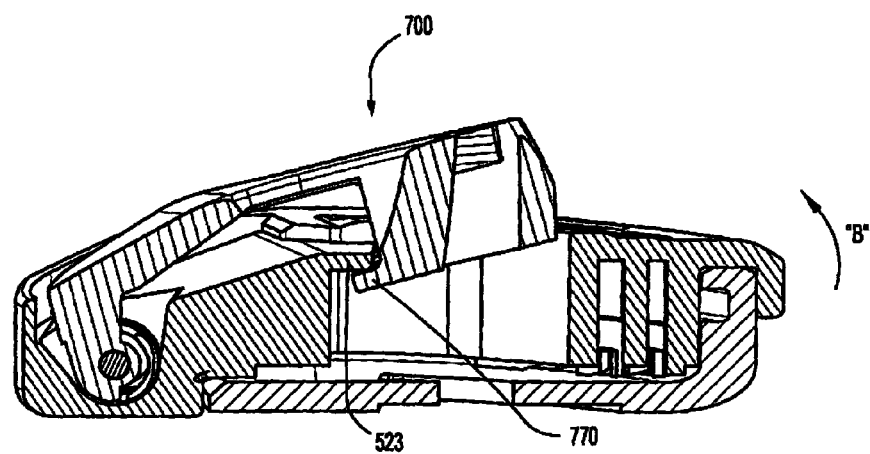
FIG. 27 is a cross-sectional view of the tissue stop of FIG. 26 coupled to the loading unit.
Figure 26:
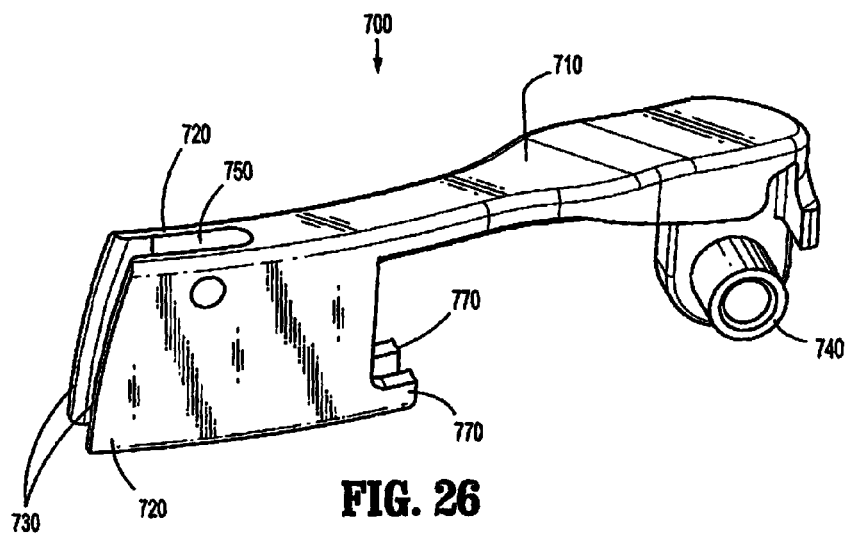
FIG. 26 is a perspective view of a tissue stop for use with the loading unit of FIGS. 3-10.

With reference to FIGS. 21 and 22, pushers 532 of the illustrated embodiments each engage two or more staples 530. Pushers 532 include a single distally-located triple pusher 532a (FIG. 23), a single proximally-located double pusher 532b (FIG. 24), and a series of triple pushers 532c (one triple pusher 532c is shown in FIG. 25) which extend between double pusher 532b and triple pusher 532a on each side of slot 526. In disclosed embodiments, portions of pushers 532a, 532b, 532c include various radii of curvature included therewith and are in the range of approximately 1.00 inches to about 1.50 inches. It is also disclosed that at least one pusher 532a, 532b, 532c includes no curved surfaces—only linearly angled surfaces.

During operation of stapler 10, actuation of its movable handle 22 through successive strokes causes distal advancement of its drive rod 30 (a distal portion of which is illustrated in FIGS. 2 and 11-13), such that drive rod 30 pushes a drive assembly 1600 through cartridge 518. (Further details of how actuation of movable handle 22 causes distal advancement of drive rod 30 are explained in U.S. Pat. No. 6,953,139 to Milliman et al., which has been incorporated by reference herein.) The movement of drive assembly 1600, and in particular, a dynamic clamping member 606 affixed thereto, moves a longitudinally curved actuation sled 536 (see FIGS. 18-20) through cartridge 518. As sled 536 moves through cartridge 518, longitudinally curved cam wedges 534 of actuation sled 536 sequentially engage pushers 532 to move pushers 532 vertically within staple retention slots 528 and eject staples 530 into staple forming depressions 514 of anvil plate 512. Subsequent to the ejection of staples 530 from retention slots 528 (and into tissue), a cutting edge 606d of dynamic clamping member 606 severs the stapled tissue as cutting edge 606d travels through curved slot 526 of cartridge 518.

Referring to FIG. 8 and in accordance with embodiments of the present disclosure, cartridge 518 includes a tissue contacting surface 540 including surfaces 540a, 540b, and 540c. Surface 540a is adjacent longitudinal slot 526 and defines a first gap between tissue contacting surface 540 and a bottom surface 544 of anvil plate 512. Surface 540b is located adjacent surface 540a and defines a second gap between tissue contacting surface 540 and bottom surface 544. Surface 540c is located proximal to an outer perimeter of cartridge 518 and defines a third gap between tissue contacting surface 540 and bottom surface 544. The first gap is less than the second gap, which is less than the third gap. When anvil 506 is approximated towards cartridge 508, layers of tissue located between bottom surface 544 and tissue contacting surface 540 are compressed. Since the first gap is the smallest, tissue located between surface 540a and bottom surface 544 is compressed the most. Similarly, the tissue located between surface 540c and bottom surface 544 is compressed the least, with the tissue located between surface 540b and bottom surface 544 being compressed to an intermediate degree. The arrangement of surfaces 540a, 540b, 540c on tissue contacting surface 540 provides a tissue compression gradient extending transverse to a longitudinal axis of the cartridge 518.

Referring to FIGS. 8, 21 and 22 in conjunction with the stepped arrangement of tissue contacting surface 540, the illustrated embodiment of staples 530 include varying leg lengths for cooperating with the varying gaps. Staples 530a have the shortest leg length and are associated with surface 540a. Similarly, staples 530b have an intermediate leg length and are associated with surface 540b, while staples 530c have the longest leg length and are associated with surface 540c. The leg length of staples 530b is between the leg length of staples 530a and 530c. Since the tissue between surface 540a and bottom surface 544 has been compressed the most, the resulting thickness of the tissue is at a minimum, thereby allowing a staple having a shorter leg length (i.e. staple 530a) to be used to join the layers of tissue. The layers of tissue between surface 540b and bottom surface 544 are compressed to an intermediate degree of compression and the resulting thickness of the tissue layers allows a staple having an intermediate leg length (i.e. staple 530b) to be used when joining the layers of tissue. The layers of tissue between surface 540c and bottom surface 544 are compressed the least amount and are thicker than the other layers requiring staples that have the longest leg length (i.e. staples 530c) for joining the layers of tissue.

In particular, the illustrated embodiment of pusher 532 includes plates 531a, 531b, 531c, which cooperate with staples 530a, 530b, 530c, respectively. Plate 531a has a height which is greater than the height of plate 531b. Additionally, the height of plate 531b is greater than the height of plate 531c. Pusher 532 further includes cam members 542 that are longitudinally staggered. As sled 536 translates distally through cartridge 518, cam wedges 534 engage cam members 542 of pusher 532, thereby urging pusher 532 in a direction transverse to the longitudinal axis of cartridge 518 and urging staples 530 towards staple forming depressions 514 of anvil plate 512. In particular, cam wedges 534 are longitudinally staggered such that when they engage staggered cam members 542, the resulting forces applied to move pusher 532 towards tissue contacting surface 540 are evenly applied.

With continued reference to FIGS. 21 and 22, staples 530a, 530b, 530c ride on pusher 532 (for illustrative purposes, pusher 532c from FIG. 25 is shown). Additionally, cam members 542 of each pusher 532 include cam surfaces 542a and 542b. Each cam surface 542a, 542b is configured to be contacted by cam wedges 534. In particular, and with reference to FIGS. 21-25, cam wedges 534a are configured to cam surfaces 542a; cam wedges 534b are configured to engage cam surfaces 542b; central section 534c of sled 536 is configured to travel through slot 526.

Referring to FIG. 20, the illustrated embodiment of actuation sled 536 includes a longitudinally curved projection 535 depending from a lower surface thereof. Projection 535 is configured to travel within a slot 515 (FIG. 10) of channel or carrier 516. In disclosed embodiments, the radius of curvature of both cam wedges 534 and projection 535 is between about 1.00 inches and about 2.00 inches, and in particular, may be approximately 1.40 inches.

With reference to FIG. 10, proximal body portion 502 includes an inner body 503 formed from molded half-sections 503a and 503b, a drive assembly 1600 and a drive locking assembly 564. Proximal body portion 502 is coupled to tool assembly 504 by a mounting assembly 570. Mounting assembly 570 has a pair of extensions 576 which extend into a proximal end of carrier 516. Each extension 576 has a transverse bore 578 which is aligned with a hole 580 in the cartridge 518 such that mounting assembly 570 is pivotally secured to cartridge 518 by pin 582. Mounting assembly 570 is fixedly secured to half-section 503a by a pair of vertical protrusions 584. Vertical protrusions 584 extend upwardly from mounting assembly 570 and frictionally fit into corresponding recesses (not shown) in half-section 503a.

With continued reference to FIG. 10, the illustrated embodiment of anvil cover 510 includes a proximally extending finger 588 having a pair of cutouts 590 formed therein. Cutouts 590 are positioned on each lateral side of finger 588 to help secure anvil cover 510 to half-section 503a. More particularly, half-section 503a includes a channel 505 therein, and channel 505 includes a pair of protrusions 505a. Finger 588 of anvil cover 510 mechanically engages channel 505 of half-section 503a, such that cutouts 590 are aligned with protrusions 505a. An outer sleeve 602 covers the finger and channel. The configuration of finger 588 and channel 505 facilitates a secure connection between anvil cover 510 and half-section 503a. Moreover, this connection results in a non-movable (e.g., non-pivotable) anvil assembly 506 with respect to proximal body portion 502.

Figure 11:
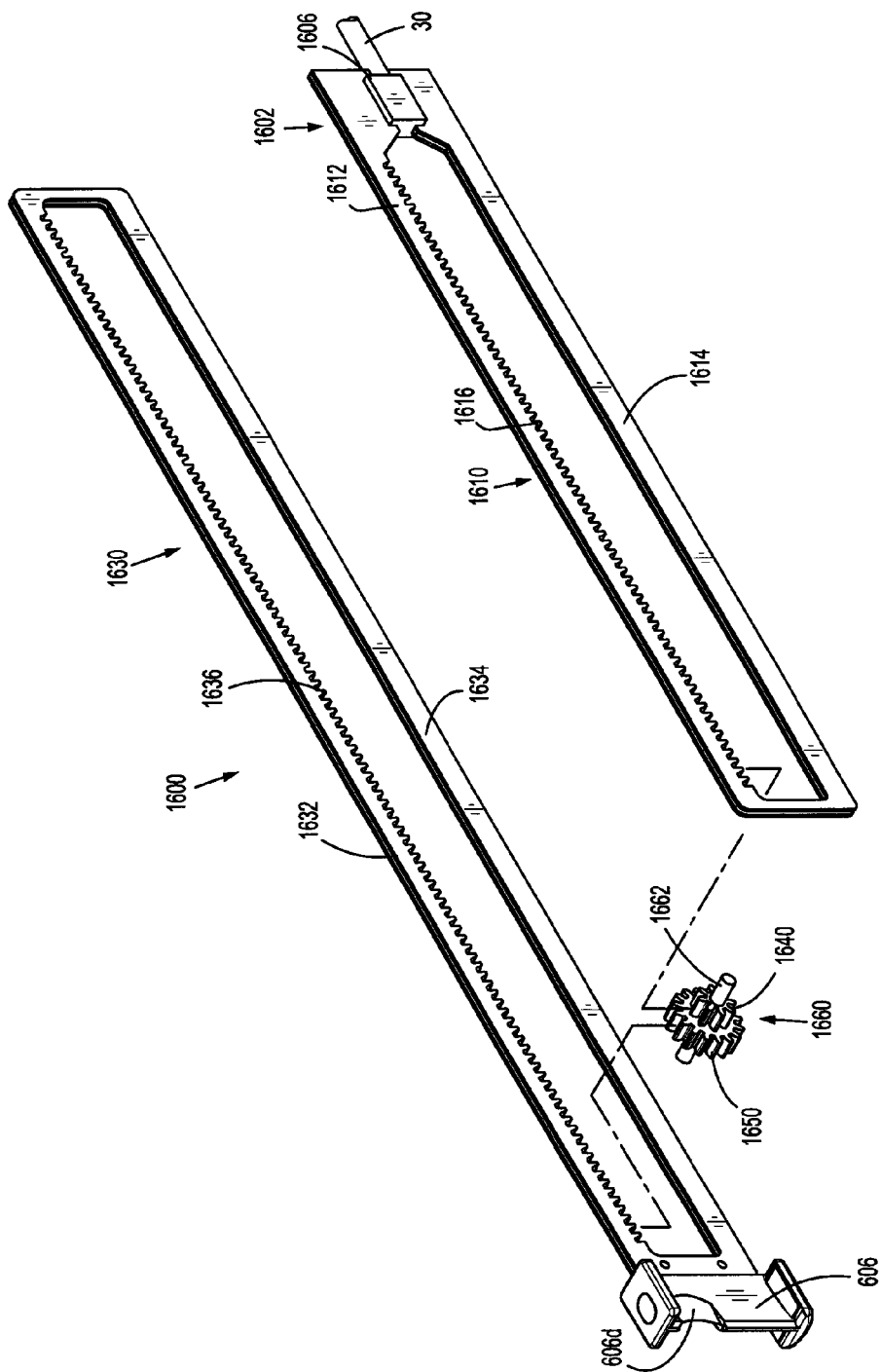
FIG. 11 is a perspective assembly view of a drive assembly and dynamic clamping member of the loading unit of FIGS. 3-10.
Figure 12:
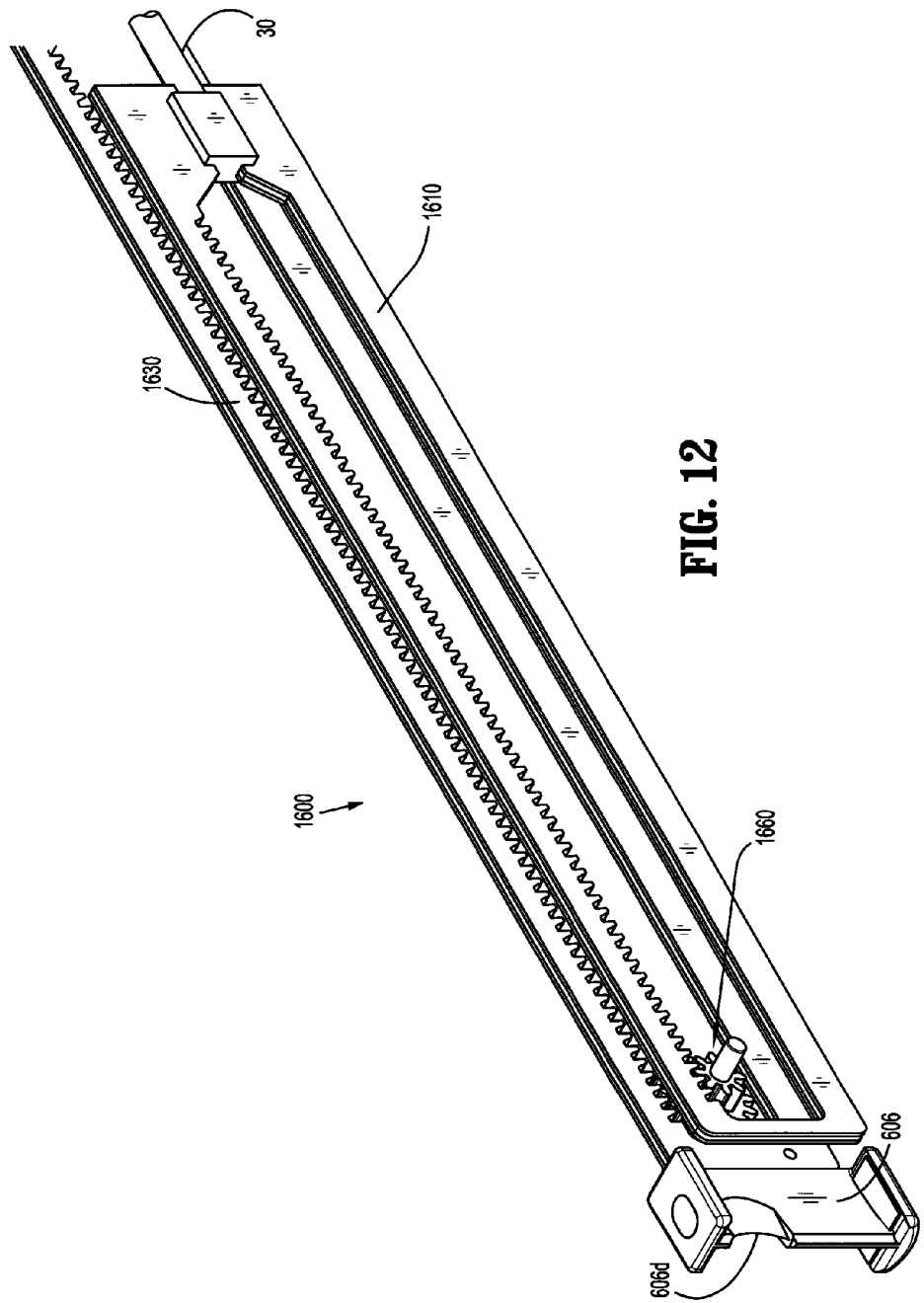
FIGS. 12 and 13 are perspective views of the assembled drive assembly of FIG. 11.
Figure 13:
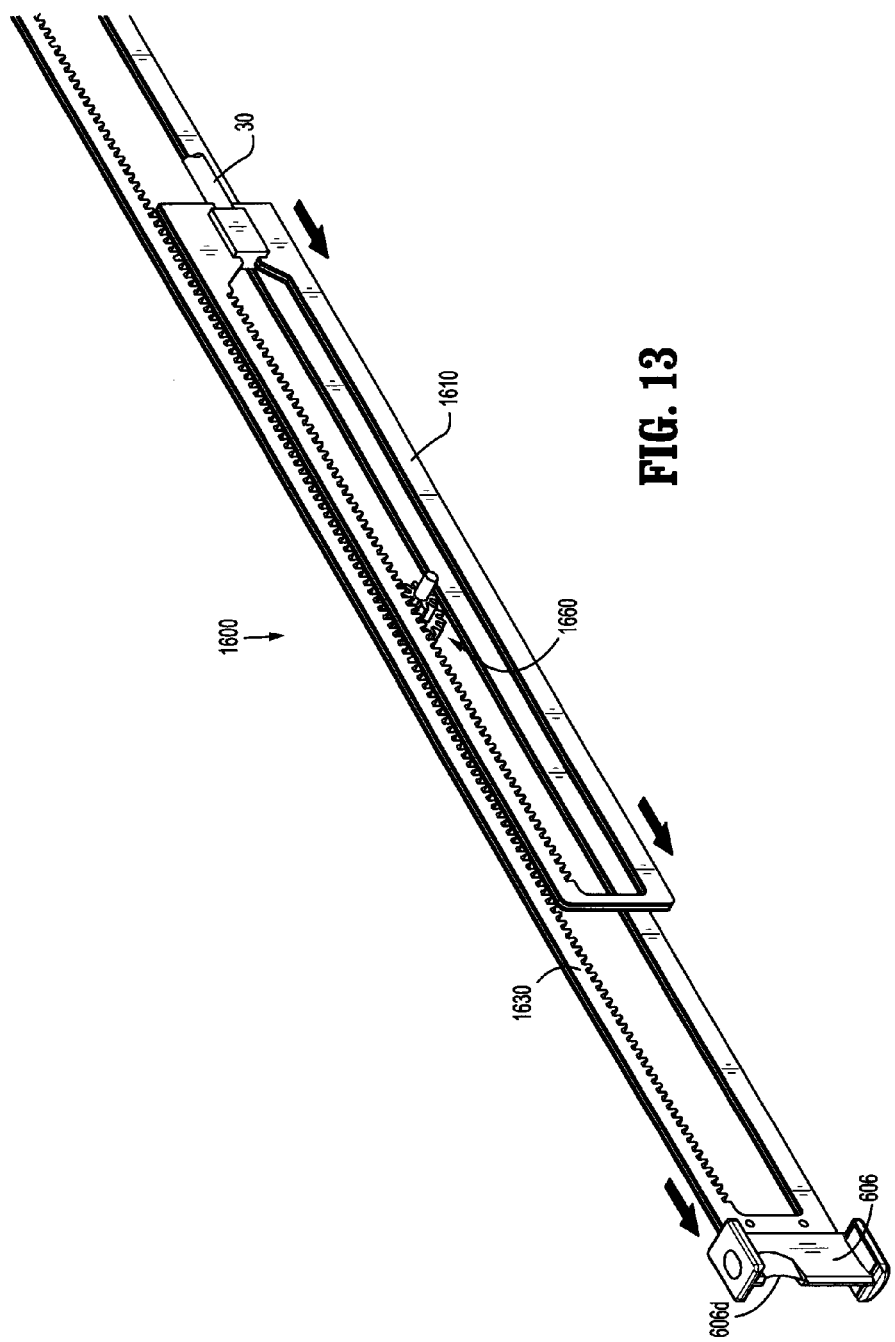
Figure 14:
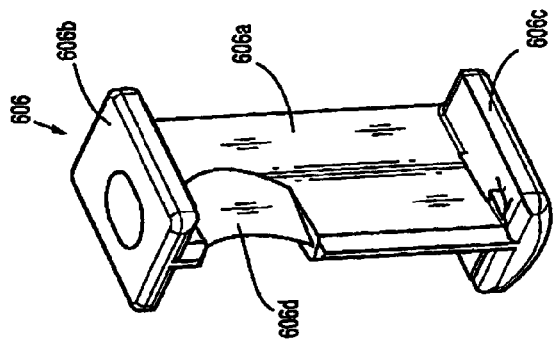
FIGS. 14-17 are various views of the dynamic clamping member according to an embodiment of the present disclosure.

With reference to FIGS. 11-13, the drive assembly 1600 includes an input portion 1610, an output portion 1640, and a gear system 1660. Input portion 1610 forms a connection with the drive rod 30, and output portion 1640 is connected to dynamic clamping member 606. Input portion 1610 is generally rectangular and includes a set of teeth 1616 thereon. Teeth 1616 are illustrated as being disposed on an upper section 1612 of input portion 1610, but it is envisioned that teeth 1616 are disposed on upper section 1612 and/or lower section 1614 of input portion 1610. Output portion 1630 is generally rectangular and includes a set of teeth 1636 thereon. Teeth 1636 are illustrated as being disposed on an upper section 1632 of output portion 1630, but it is envisioned that teeth 1636 are disposed on upper section 1632 and/or lower section 1634 of output portion 1630.

Gear system 1660 includes an input gear 1640 and an output gear 1650. The input gear 1640 is configured to mesh with the teeth 1616 of input portion 1610 of the drive assembly 1600. The output gear 1650 is configured to mesh with the teeth 1636 of output portion 1630 of the drive assembly 1600. Gear system 1660 also includes shaft 1662 that extends through centers of input gear 1640 and output gear 650, and which is attached to the input gear 1640 and the output gear 1650. The shaft 1662 is rotationally supported within the inner body 503 of the proximal body portion 502 (i.e., the shaft 1662 can rotate with respect to the proximal body portion 502, but the shaft 1662 is restrained from longitudinal movement with respect to the proximal body portion 502).

In use, distal movement of drive rod 30 causes distal movement of input portion 1610 of the drive assembly 1600. Distal movement of the input portion 1610 causes rotation of input gear 1640. Rotation of input gear 1640 causes rotation of output gear 1650, which in turn, causes distal movement of the output portion 1630 of the drive assembly 1600. Additionally, and as can be appreciated, proximal movement of the input portion 1610 causes proximal movement of the output portion 1630. The gear ratio of the gear system 1660 is defined by the number of teeth on the output gear 1650 divided by the number of teeth on the input gear 1640.

As can be appreciated, the gear ratio of the gear system 1660 can be designed such that distal travel of the output portion 1630 of the drive assembly 1600 is equal to about twice the distal travel of the input portion 1610 of the drive assembly 1600, for example. Utilizing such a gear ratio increases the amount of distal travel of the dynamic clamping member 606 in response to a typical (e.g., single) actuation of the movable handle 22.

It is envisioned that the gear ratio is anything greater than 1:1, e.g., 1.25:1, 1.5:1, 1.75:1, 2:1, etc. Other gear ratios are also contemplated by the present disclosure. To obtain a desired gear ratio, the number of teeth on the input gear 1640 and/or the output gear 1650 is engineered accordingly.

At least a portion of drive assembly 1600 is sufficiently flexible to be advanced through the curvature of the tool assembly 504. Engagement section 1602 is fastened to a proximal portion of input portion 1610. A proximal end of engagement section 1602 includes diametrically opposed inwardly extending fingers 1606. Fingers 1606 engage a hollow drive member 1608 to fixedly secure drive member 1608 to the proximal end of input portion 1610. Drive member 1608 defines a proximal porthole which receives the distal end of a control rod of drive rod 30 (see FIGS. 2 and 11-13) when loading unit 500 is attached to surgical stapling instrument 10.

Figure 16:
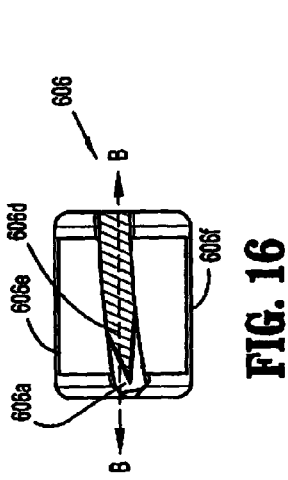
Figure 15:
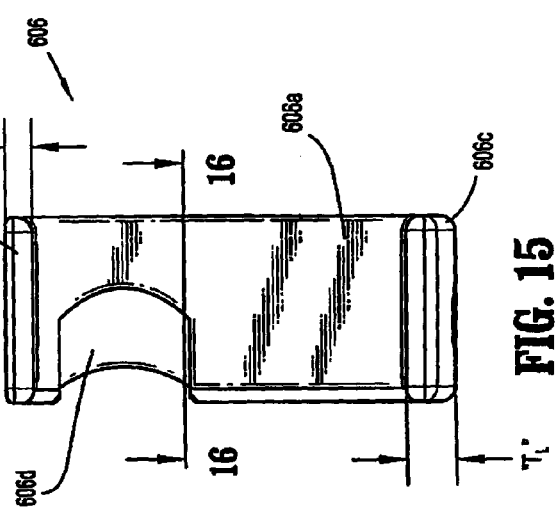

With reference to FIGS. 14-17, dynamic clamping member 606 includes a vertical strut 606a, an upper beam 606b and a lower beam 606c. A knife or cutting edge 606d is formed on a distal face of vertical strut 606a. As illustrated, the width of vertical strut 606a is equal to the width of drive beam 604 of drive assembly 1600 (see FIG. 12). With particular reference to FIG. 16, vertical strut 606a and knife 606d are longitudinally curved from a first lateral side 606e of clamping member towards a second lateral side 606f of clamping member 606. Both upper beam 606b and lower beam 606c are linearly disposed with respect to longitudinal axis "A-A."

As illustrated in FIGS. 14-17A, the present disclosure includes embodiments of dynamic clamping member 606 that are asymmetrical. For instance, in the embodiment illustrated in FIGS. 15 and 17, lower beam 606c is thicker than upper beam 606b. In this embodiment, dynamic clamping member 606 is asymmetrical about horizontal axis "H-H" illustrated in FIG. 17. It is envisioned that lower beam 606c includes a thickness "$T_L$", which is between about 0.050 inches and about 0.100 inches, and in particular, may be approximately 0.068 inches. It is envisioned that upper beam 606b includes a thickness "$T_U$", which is between about 0.025 inches and about 0.050 inches, and in particular, is approximately 0.037 inches.

Figure 17:
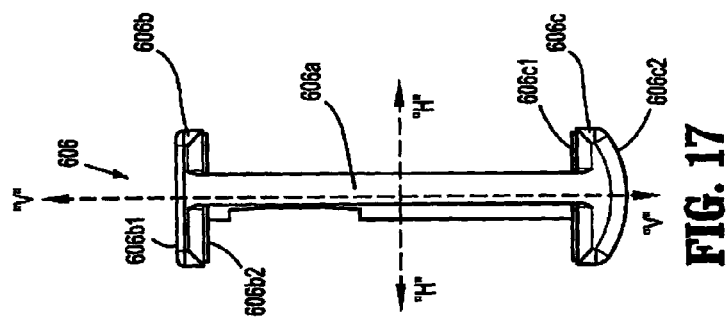

An additional example of an asymmetrical dynamic clamping member 606 is also illustrated in FIG. 17. In this embodiment, the transverse cross-sectional shape of upper beam 606b includes an upper planar surface 606b1 and a lower planar surface 606b2. The cross-sectional shape of lower beam 606c includes an upper planar surface 606c1 and a lower arcuate surface 606c2. In this embodiment, dynamic clamping member 606 is asymmetrical about the horizontal axis "H-H."

The embodiment shown in FIGS. 16 and 17 illustrates proximal portion of vertical strut 606a being off-center with respect to the remainder of clamping member 606. More particularly, it is envisioned that the center of vertical strut 606a is between about 0.070 inches and about 0.090 inches (e.g., approximately 0.080 inches) from first lateral side 606e of clamping member 606, and is between about 0.90 inches and about 0.110 inches (e.g., approximately 0.100 inches) from second lateral side 606f of clamping member 606. In this embodiment, dynamic clamping member 606 is asymmetrical about vertical axis "V-V" illustrated in FIG. 17.

With reference to FIG. 17A, dynamic clamping member 606' is shown. Lower beam 606c' is wider than upper beam 606b' of dynamic clamping member 606'. More particularly, it is envisioned that a width "wl" of lower beam 606c' is between about 0.180 inches and about 0.200 inches, and that a width "wu" of upper beam 606b' is between about 0.160 inches and about 0.180 inches. In this embodiment, dynamic clamping member 606' is asymmetrical about the horizontal axis "H-H." Further, while not explicitly shown, it is envisioned that upper beam 606b' is wider than lower beam 606c' of a dynamic clamping member 606 of the present disclosure. Additionally, dynamic clamping member 606' is shown as being longitudinally linear (vis-à-vis longitudinally curved), in accordance with embodiments of the present disclosure.

The asymmetrical embodiments of dynamic clamping member 606 of the present disclosure help ensure proper orientation of dynamic clamping member 606 during assembly of surgical stapling instrument 10 or loading unit 500. That is, the asymmetry of dynamic clamping member 606 prevents dynamic clamping member 606 from improper placement with respect to tool assembly 504, since dynamic clamping member 606 can only physically fit in a particular orientation. In particular, the asymmetry ensures that knife 606d faces distally and is positioned to travel through the space between cartridge assembly 508 and anvil assembly 506, for example.

With reference to FIG. 17B, the present disclosure includes another embodiment of a dynamic clamping member 606" that is also configured to help ensure proper orientation of dynamic clamping member 606" during assembly of surgical stapling instrument 10 or loading unit 500. Dynamic clamping member 606" includes a protrusion 607 extending from a proximal surface 606i thereof. In the illustrated embodiment, a drive assembly 1600" has a smaller height than embodiment of drive assembly 1600' illustrated in FIGS. 10-13. Protrusion 607 is shown being disposed on a lower portion of dynamic clamping member 606" (i.e., on the opposite side as cutting edge 606d") and to one side of drive assembly 1600", but it is envisioned that protrusion 607 is disposed on the other side of drive assembly 1600".

As discussed above, the inclusion of protrusion 607 helps ensure proper orientation of dynamic clamping member 606". More particularly, it is envisioned that extensions 576 of mounting assembly 570 would physically prevent further assembly of dynamic clamping member 606" being incorrectly fastened to drive assembly 1600" (e.g., when dynamic clamping member 606" is up-side-down with respect to drive assembly 1600".

It is further envisioned that dynamic clamping member 606, 606' may include any combination of the asymmetrical features discussed herein and may also include protrusion 607 of dynamic clamping member 606".

With additional reference to dynamic clamping member 606 of FIGS. 14-17A, it is envisioned that each of upper beam 606b and 606c includes a plastic material or layer which is injection molded onto an outwardly facing surface of each beam 606b and 606c. Plastic layer provides reduced frictional engagement between dynamic clamping member 606 and cartridge and anvil assemblies 508 and 506, respectively, during actuation of tool assembly 504.

Referring back to FIG. 8, channel 511 is configured and dimensioned accordingly to accommodate a corresponding embodiment of upper beam 606b of clamping member 606; slot 526 is configured and dimensioned accordingly to accommodate a corresponding embodiment of vertical strut 606a of clamping member 606. As can be appreciated, when used with the embodiment of dynamic clamping member 606 of FIG. 17A, channel 511 is too narrow to accommodate lower beam 606c of dynamic clamping member 606.

With reference to FIG. 10, when drive assembly 1600 is advanced distally within tool assembly 504, upper beam 606b moves within channel 511 defined between anvil plate 512 and anvil cover 510, and lower beam 606c moves over an exterior surface of carrier 516. When lower beam 606c engages and moves over cam surface 516a, cartridge assembly 508 pivots from the open position to the closed position. As dynamic clamping member 606 continues to move distally along and through tool assembly 504, the maximum gap between anvil plate 512 and cartridge 518 is defined by engagement of layer 606e on upper beam 606b (FIG. 14 and a lower surface defining channel 511, and engagement of a layer 606g on lower beam 606c with the external surface of carrier 516. In disclosed embodiments, the height of channel 511 is greater than the height of upper beam 606b, providing clearance between the upper surface of dynamic clamping member 606 and the anvil plate 512 so that upper beam 606b of dynamic clamping member 600 does not simultaneously engage the upper and lower surfaces of anvil channel 511.

With continued reference to FIG. 10, loading unit 500 includes a locking mechanism 564 including a locking member 620 and a locking member actuator 622. Locking member 620 is rotatably supported within a longitudinal or axial slot 625 formed in a proximal portion of an upper housing half 503a of inner body 503 of loading unit 500. Locking member 620 is movable from a first position, in which locking member 620 maintains drive assembly 1600 in a prefired position, to a second position in which drive assembly 1600 is free to move axially.

Locking member 620 includes a semi-cylindrical body 624 which is slidably positioned within transverse slot 625 formed in upper housing half 503a of body portion 503. Body 624 includes a radially inwardly extending cam member 628 and a radially inwardly extending finger 630. Finger 630 is dimensioned to be received within a notch 632 formed in drive assembly 1600. Engagement of finger 630 in notch 632 of drive assembly 1600 prevents drive assembly 1600 from moving linearly within body portion 503 to prevent actuation of loading unit 500 prior to attachment of loading unit 500 to surgical instrument 10.

Locking member actuator 622 is slidably positioned within axial slot 625 formed in upper housing half section 503a of body portion 503 of loading unit 500. Actuator 622 includes a proximal abutment member 636, a distal spring guide 627, and a central cam slot 640. Axial slot 641 in the housing half section 503a intersects transverse slot 625 such that cam member 628 of locking member 620 is slidably positioned within cam slot 640 of locking member actuator 622. A biasing member or spring 642 is positioned about spring guide 627 between a distal surface of actuator 622 and a wall 641a defining the distal end of axial slot 641. Spring 642 urges actuator 622 to a first position within axial slot 641. In the first position, abutment member 636 is positioned on insertion tip 650 of proximal body portion 502 (FIG. 3) and cam slot 640 is positioned to locate cam member 628 such that finger 630 of lock member 620 is positioned within notch 632 of drive assembly 1600.

Prior to attachment of loading unit 500 onto surgical instrument 10, spring 642 urges actuator 622 to the first position to maintain the lock member 620 in its first position as discussed above. When insertion tip 650 of loading unit 500 is linearly inserted into the open end of the body portion 18 (FIG. 2) of surgical instrument 10, nubs 652 of insertion tip 650 (FIG. 3) move linearly through slots (not shown) formed in open end of body portion 18. As nubs 652 pass through the slots, the proximal end of abutment member 636, which is angularly offset from nubs 652, abuts a wall defining the slots for receiving nubs. As loading unit 500 is moved farther into body portion, locking member actuator 622 is moved from its first position to its second position. As actuator 622 is moved to its second position, lock member 620 is cammed from its first position engaged with notch 632 of drive assembly 1600 to its second position to move finger 630 from notch 632. The locking mechanism including locking member 620 and locking member actuator 622 prevents advancement of the drive assembly 1600 of loading unit 500 prior to loading of loading unit 500 onto a surgical instrument 10.

Figure 3:
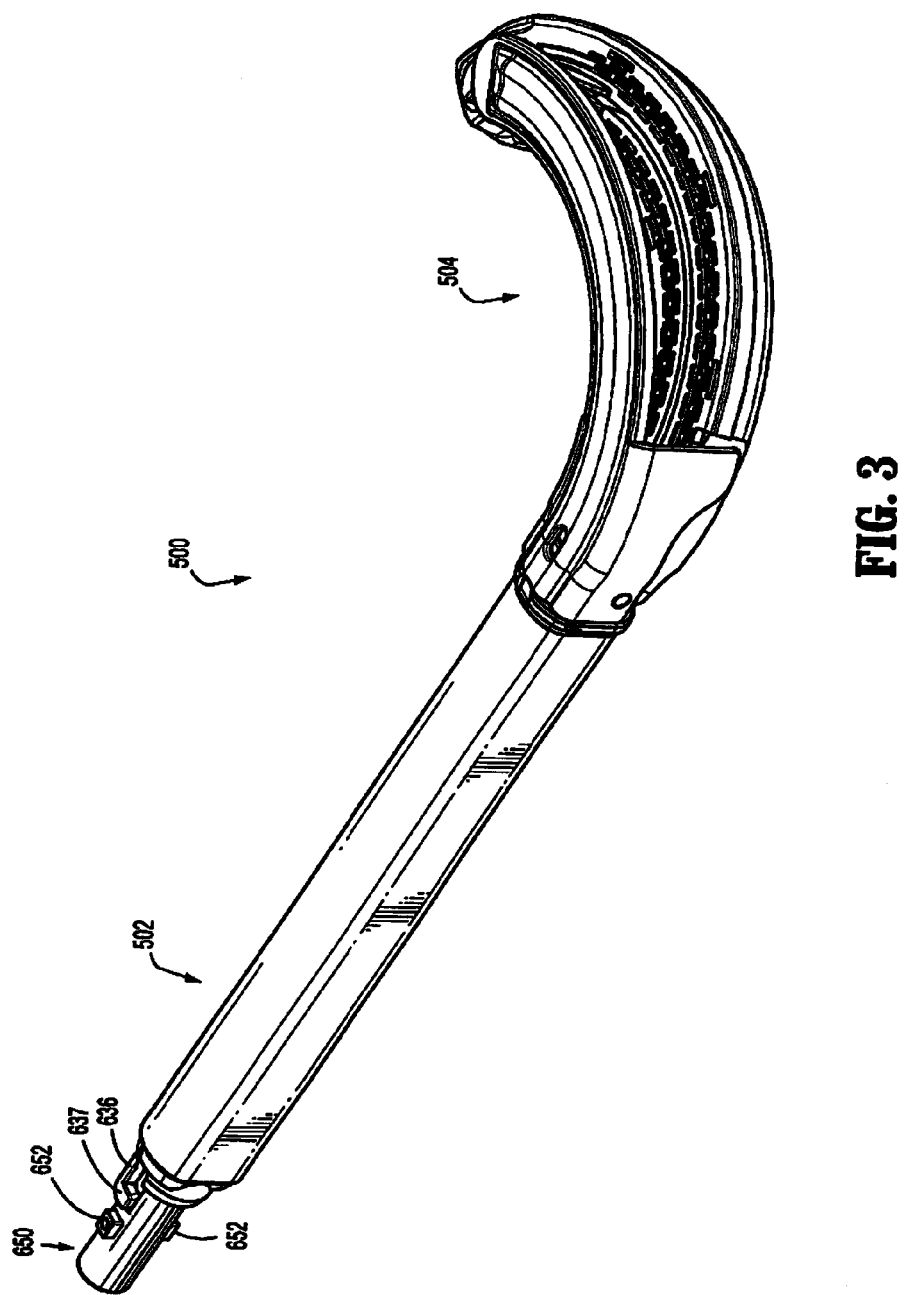
FIG. 3 is a perspective view of the loading unit of FIGS. 1 and 1A.

In the embodiments illustrated in FIGS. 3 and 10, locking member actuator 622 includes an articulation lock portion 637 disposed thereon. In particular, articulation lock portion 637 extends in an approximate right angle from abutment member 636. Articulation lock portion 637 is configured to physically prevent the longitudinal translation of an articulation member (not shown) of a handle portion of a surgical instrument having articulation capabilities. That is, even when loading unit 500 is engaged with a surgical instrument 10 that is otherwise capable of articulation (i.e., pivotable movement of the jaw members with respect to the elongated portion 18), articulation lock portion 637 of loading unit 500 prevents an articulation member from entering loading unit 500.

Referring to FIG. 10, upper half-section 503a of proximal body portion 502 defines a longitudinal slot 660 which receives a leaf spring 662. Leaf spring 662 is confined within slot 660 by outer sleeve 602. Leaf spring 662 has an angled proximal end 664 which is positioned to abut shoulder 1604 (FIG. 11) of engagement section 1602 of drive assembly 1600 when drive assembly 1600 is in its retracted position. When drive assembly 1600 is advanced distally by advancing drive rod 30, as described above, leaf spring 662 is flexed upwardly by shoulder 1604 of drive assembly 1600 to permit distal movement of drive assembly 1600.

Referring to FIGS. 4, 7, and 26-30, loading unit 500 also includes a tissue stop 700. Tissue stop 700 includes a body 710, a pair of legs 720 extending proximally from the body 710, a stopping portion 730, a pair of laterally opposed protrusions 740 extending transversely from body 710 (See FIG. 26), and a knife channel 750 disposed between pair of legs 720. Tissue stop 700 is pivotally connected to a distal portion of cartridge assembly 508 via the engagement between protrusions 740 and a corresponding pair of apertures (not shown) disposed within cartridge assembly 508. Cartridge assembly 508 includes an opening 519 (FIGS. 7 and 10) adapted to receive both legs 720 of tissue stop 700. A recess 521 is positioned distally of opening 519 and is adapted to receive a portion of tissue stop 700 therein. The recess 521 and opening 519 are shown in FIG. 10.

Figure 4:
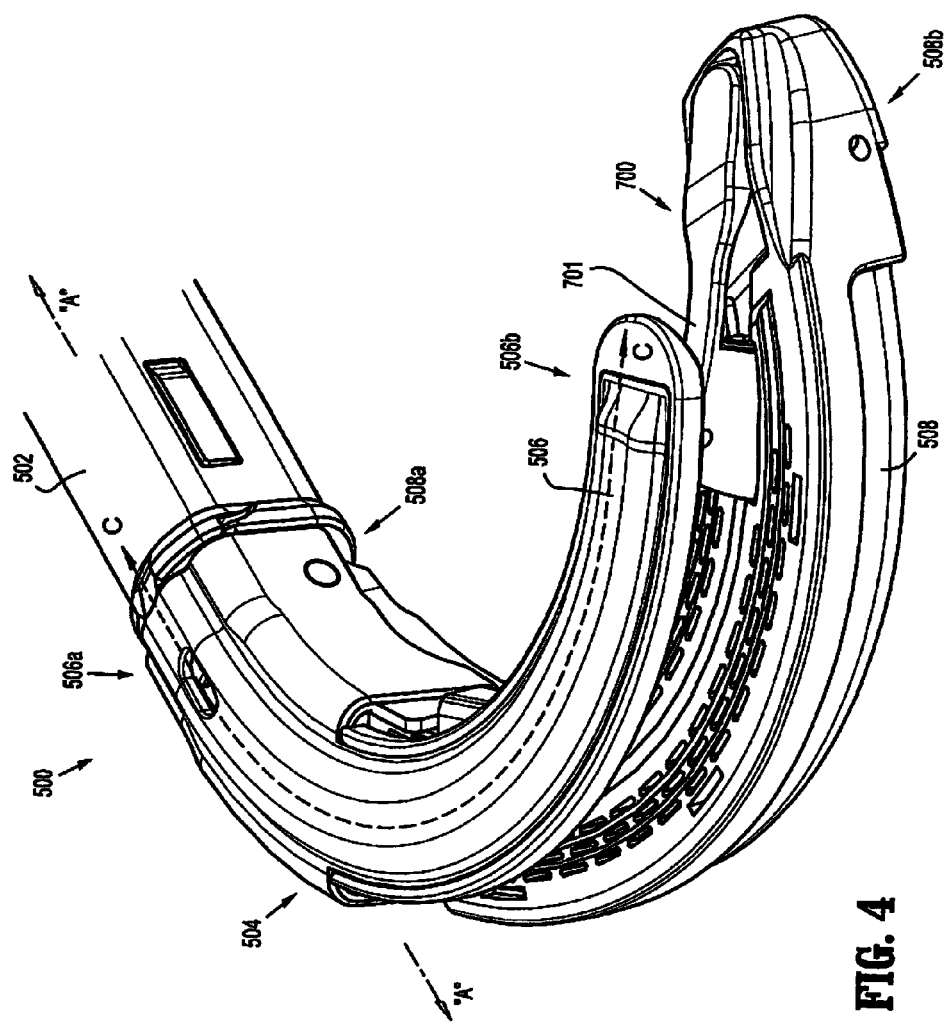
FIG. 4 is an enlarged view of the area of detail of FIGS. 1 and 1A.

Tissue stop 700 is movable between a first position (FIG. 4), which corresponds to when the jaw members are in an open position where an upper surface 701 thereof is disposed between cartridge assembly 508 and anvil assembly 506 (FIG. 4 illustrates the jaw members in a partially approximated position; FIG. 6 illustrates the jaw members in a fully opened position), and a second position (FIG. 30), which corresponds to when the jaw members are in the approximated position and where upper surface 701 of tissue stop 700 is substantially flush with tissue contacting surface 514 of cartridge 518. (In FIG. 30, upper surface 701 is hidden as upper surface 701 is within cartridge assembly 508.) A biasing member 760 (FIG. 10), a portion of which is disposed around protrusion 740, urges tissue stop 700 towards its first position. Tissue stop 700 also includes a finger 770 (FIG. 26) extending distally from each leg 720. With specific reference to FIG. 27, when the jaw members are in the open position, fingers 770 of tissue stop 700 engage a lip 523 disposed on cartridge assembly 508 to limit the amount of movement imparted by biasing member 760 in the general direction of arrow "B" in FIG. 27.

Figure 28:
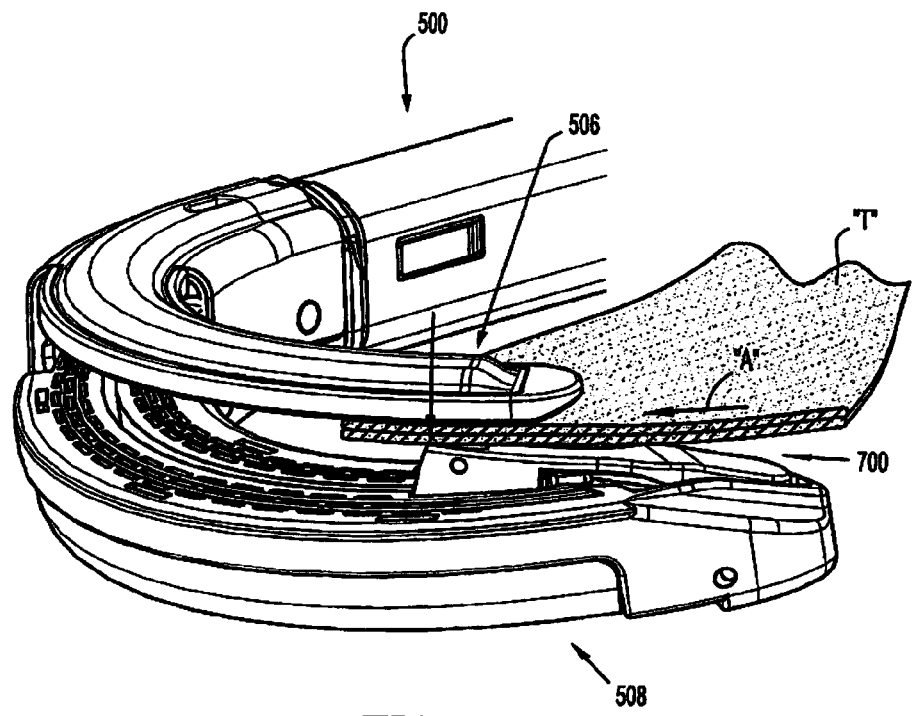
FIGS. 28-30 are perspective views of the loading unit of FIGS. 3-10 interacting with a layer of tissue at various stages of operation of the loading unit.
Figure 29:
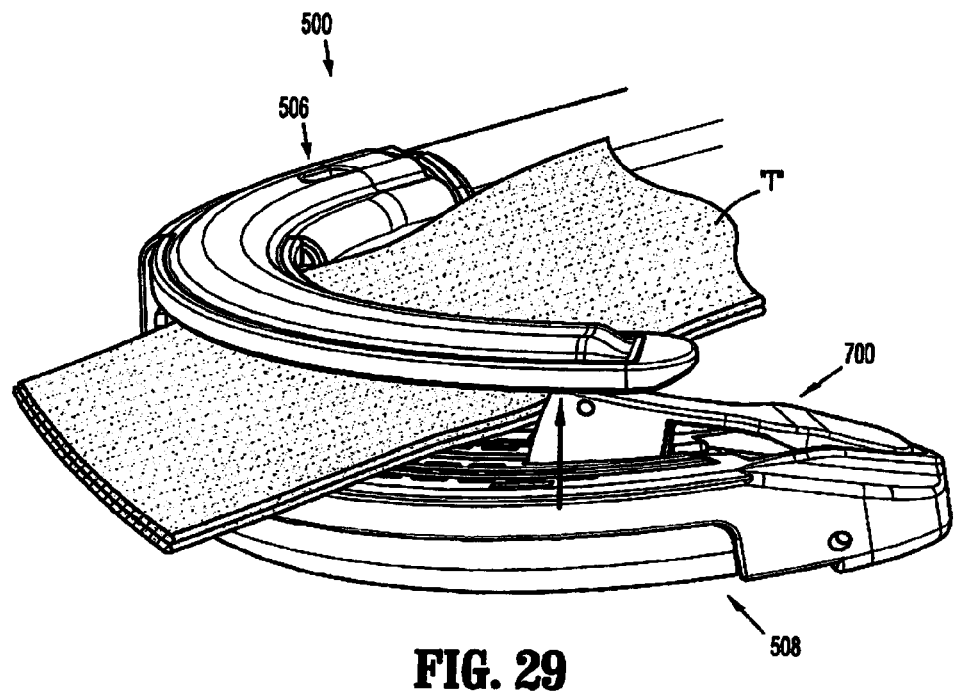
Figure 30:
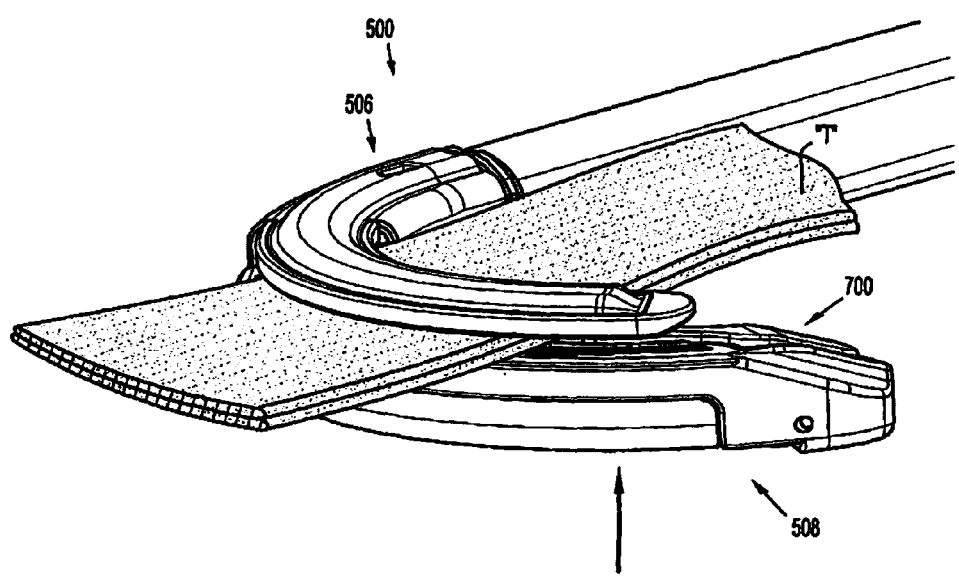

When tissue stop 700 is in its first position, tissue "T" is proximally insertable (in the general direction of arrow "A" in FIG. 28) from distally beyond tissue stop 700, to a location that is between anvil assembly 206 and cartridge assembly 508 and proximal of tissue stop 700 (see FIGS. 28 and 29). In this position, stopping portion 730, which is disposed at an oblique angle (e.g., between about 45° and about 90°) with respect to tissue contacting 540 of cartridge assembly 508, impedes tissue from distally escaping the tool assembly 504. When the jaw members are approximated (e.g., when cartridge assembly 508 is pivoted towards anvil assembly 506), tissue stop 700 (or tissue "T") contacts anvil assembly 506, thus causing tissue stop 700 to pivot from its first position towards its second position. Legs 720 of tissue stop 700 are configured to lie within opening 519 (i.e., equal to or below the tissue contacting surface 540) of cartridge assembly 508 when tissue stop 700 is in its second position, such that legs 720 do not interfere with the location of the tissue with respect to the cartridge assembly 508 and respect to anvil assembly 506 (i.e., so that the staples can be deployed into tissue lying over the tissue stop). When the cartridge assembly 508 moves away from anvil assembly 506, tissue stop 700, under the influence of biasing member 760, returns to its first position.

With additional regard to knife channel 750, knife channel 750 is configured to allow vertical strut 606a (including cutting edge 606d) of dynamic clamping member 606 to travel distally past a portion of tissue stop 700 (i.e., at least to a location adjacent the distal-most longitudinal slot 528). Additionally, it is envisioned that at least a portion of knife channel 750 (e.g., the portion that is contacted by cutting edge 606d) is over molded with plastic or another suitable material.

While not explicitly illustrated, it is also envisioned that drive assembly 1600 is usable with a surgical instrument having parallel jaws. An example of a surgical instrument having parallel jaws is described in commonly-owned U.S. Pat. No. 7,237,708 to Guy et al., the entire contents of which are hereby incorporated by reference herein.

The present disclosure also relates methods of using the described surgical instrument 10 or loading unit 500 to perform a lower anterior resection. Such a method includes providing surgical instrument 10 or loading unit 500, positioning jaw members adjacent tissue, approximating one jaw member (e.g., cartridge assembly 508) with respect to the other jaw member (e.g., anvil assembly 506), advancing drive assembly 1600 such that dynamic clamping member 606 and at least a portion of drive assembly 1600 move along a curvilinear path to cause staples 530 to be ejected into tissue "T" and to cut tissue "T." In certain embodiments, the jaw members are approximated, and the interior of the intestinal tissue is then washed out or otherwise cleansed. The tissue is then cut and stapled. In this way, the interior intestinal tissue is cleansed up to the location of the jaw members.

With particular reference to FIG. 31, a transverse cross-sectional view of surgical instrument 10 (e.g., loading unit) taken along a portion of actuation sled 536 is shown. The jaw members of surgical instrument 10 are shown and include an anvil assembly 506 and a cartridge assembly 508, which includes a channel or carrier 516. Here, actuation sled 536 includes a projection 535 depending from a lower surface thereof. (FIG. 20 also illustrates actuation sled 536 having projection 535 depending from a lower surface thereof.) Projection 535 is configured to travel within a slot 515 of a carrier 516. As actuation sled 536 is translated distally, projection 535 helps ensure that actuation sled 536 follows the curvature of the jaw members.

While the above description contains many specifics, these specifics should not be construed as limitations on the scope of the present disclosure, but merely as illustrations of various embodiments thereof. Therefore, the above description should not be construed as limiting, but merely as exemplifications of various embodiments. Those skilled in the art will envision other modifications within the scope and spirit of the claims appended hereto.

The invention claimed is:

1. A surgical instrument for surgically joining tissue, the surgical instrument comprising:
    a handle assembly;
    an elongated portion extending distally from the handle assembly and defining a longitudinal axis;
    a drive rod extending distally from the handle assembly and extending at least partially through the elongated portion;
    an end effector disposed adjacent a distal portion of the elongated portion, the end effector including a first jaw member and a second jaw member, at least one jaw member being movable with respect to the other jaw member between spaced and approximated positions; and
    a drive assembly, a proximal end of the drive assembly disposed in mechanical cooperation with a distal end of the drive rod, and a distal portion of the drive assembly disposed in mechanical cooperation with the end effector, the drive assembly including an input portion, an output portion and a gear system disposed therebetween, the gear system including an input gear configured to engage the input portion of the drive assembly, and an output gear configured to engage the output portion of the drive assembly, and wherein the gear ratio of the output gear to the input gear is greater than 1:1.

2. The surgical instrument of claim 1, wherein the handle assembly is mechanically engaged with the drive rod such that actuation of the a portion of the handle assembly causes distal translation of the drive rod, and wherein the input portion of the drive assembly is configured to mechanically engage a distal portion of the drive rod.

3. The surgical instrument of claim 1, wherein the output portion of the drive assembly is affixed to a dynamic clamping member, the dynamic clamping member being configured to eject fasteners from the first jaw member.

4. The surgical instrument of claim 1, wherein the input portion of the drive assembly includes a plurality of teeth, and wherein the output portion of the drive assembly includes a plurality of teeth.

5. The surgical instrument of claim 4, wherein the gear system includes an input gear including teeth, and wherein the teeth on the input portion of the drive assembly are configured to engage the teeth of the input gear.

6. The surgical instrument of claim 5, wherein the gear system includes an output gear including teeth, and wherein the teeth on the output portion of the drive assembly are configured to engage output teeth of output gear.

7. The surgical instrument of claim 6, wherein the input gear and the output gear are fixed together.

8. The surgical instrument of claim 6, wherein the gear ratio of the output gear to the input gear is between about 1.25:1 to about 2:1.

9. The surgical instrument of claim 1, wherein the end effector is curved with respect to the longitudinal axis.

10. A tool assembly for use with a surgical instrument having a drive rod, the tool assembly comprising:
    an end effector including a first jaw member and a second jaw member, the first jaw member being movable with respect to the second jaw member between spaced and approximated positions; and
    a drive assembly, a proximal end of the drive assembly being configured to engage a distal portion of a drive rod of a surgical instrument, a distal portion of the drive assembly being disposed in mechanical cooperation with the end effector, the drive assembly including an input portion, an output portion and a gear system disposed therebetween, the gear system including an input gear configured to engage the input portion of the drive assembly, and an output gear configured to engage the output portion of the drive assembly, and wherein the gear ratio of the output gear to the input gear is greater than 1:1.

11. The tool assembly of claim 10, wherein the input portion of the drive assembly is configured to mechanically engage a distal portion of a drive rod of the surgical instrument.

12. The tool assembly of claim 10, wherein the output portion of the drive assembly is affixed to a dynamic clamping member, the dynamic clamping member being configured to eject fasteners from the first jaw member.

13. The tool assembly of claim 10, wherein the input portion of the drive assembly includes a plurality of teeth, and wherein the output portion of the drive assembly includes a plurality of teeth.

14. The tool assembly of claim 13, wherein the gear system includes an input gear including teeth, and wherein the teeth on the input portion of the drive assembly are configured to engage the teeth of the input gear.

15. The tool assembly of claim 14, wherein the gear system includes an output gear including teeth, and wherein the teeth on the output portion of the drive assembly are configured to engage output teeth of output gear.

16. The tool assembly of claim 15, wherein the input gear and the output gear are fixed together.

17. The tool assembly of claim 15, wherein the gear ratio of the output gear to the input gear is between about 1.25:1 to about 2:1.

18. The tool assembly of claim 10, wherein the end effector includes a longitudinally curvilinear shape.

* * * * *